(12) United States Patent
Ryan et al.

(10) Patent No.: US 8,206,427 B1
(45) Date of Patent: Jun. 26, 2012

(54) APPARATUS AND METHODS FOR ENDOLUMINAL GRAFT PLACEMENT

(75) Inventors: Timothy J. Ryan, Los Altos Hills, CA (US); Thomas J. Fogarty, Portola Valley, CA (US); Jay A. Lenker, Laguna Beach, CA (US); Kirsten Freislinger, Palo Alto, CA (US)

(73) Assignee: Medtonic Vascular, Inc., Santa Rosa, CA (US)

( * ) Notice: Subject to any disclaimer, the term of this patent is extended or adjusted under 35 U.S.C. 154(b) by 1192 days.

(21) Appl. No.: 08/463,836

(22) Filed: Jun. 5, 1995

Related U.S. Application Data

(62) Division of application No. 08/255,681, filed on Jun. 8, 1994, now abandoned.

(51) Int. Cl.
*A61F 2/06* (2006.01)

(52) U.S. Cl. ................................ 623/1.11; 623/1.35

(58) Field of Classification Search .............. 606/191, 606/194, 195, 198, 108, 151–156, 200; 623/1, 623/11, 12, 1.1–1.54; 604/8
See application file for complete search history.

(56) References Cited

U.S. PATENT DOCUMENTS

| | | |
|---|---|---|
| 3,657,744 A | 4/1972 | Ersek |
| 3,868,956 A | 3/1975 | Alfidi et al. |
| 3,878,565 A | 4/1975 | Sauvage |
| 3,890,977 A | 6/1975 | Wilson |
| 3,945,052 A | 3/1976 | Liebig |
| 3,996,938 A | 12/1976 | Clark, III |
| 4,140,126 A | 2/1979 | Choudhury |
| 4,149,911 A | 4/1979 | Clabburn |
| 4,214,587 A | 7/1980 | Sakura, Jr. |
| 4,225,979 A | 10/1980 | Rey et al. |
| 4,276,874 A | 7/1981 | Wolvek et al. |
| 4,306,318 A | 12/1981 | Mano et al. |
| 4,310,354 A | 1/1982 | Fountain et al. |
| 4,416,028 A | 11/1983 | Eriksson et al. |
| 4,425,908 A | 1/1984 | Simon |
| 4,503,569 A | 3/1985 | Dotter |
| 4,505,767 A | 3/1985 | Quin |
| 4,512,338 A | 4/1985 | Balko et al. |
| 4,545,082 A | 10/1985 | Hood |
| 4,553,545 A | 11/1985 | Maass et al. |
| 4,560,374 A | 12/1985 | Hammerslag |
| 4,562,596 A | 1/1986 | Kornberg |

(Continued)

FOREIGN PATENT DOCUMENTS

AU    B-79604/91    8/1993

(Continued)

OTHER PUBLICATIONS

Product Brochure—"*Memotherm Ilica Stents*", pp. 1-6.

(Continued)

*Primary Examiner* — Kathleen Sonnett

(57) ABSTRACT

A vascular graft comprises a perforate tubular compressible frame having a fabric liner disposed over at least a portion of the frames lumen. The graft may be used in combination with a base structure to form a bifurcated graft in situ. The base structure compresses a compressible frame having a fabric liner which defines a pair of divergent legs. The base structure is positioned within the aorta so that one leg enters each iliac. The tubular grafts can then be introduced into each leg to form the bifurcated structure. A graft delivery catheter includes a controllably flared sheath which facilitates recapture of a partially deployed graft.

42 Claims, 14 Drawing Sheets

U.S. PATENT DOCUMENTS

| | | | |
|---|---|---|---|
| 4,577,631 A | 3/1986 | Kreamer |
| 4,577,632 A | 3/1986 | Grasset |
| 4,580,568 A | 4/1986 | Gianturco |
| 4,617,932 A | 10/1986 | Kornberg |
| 4,629,458 A | 12/1986 | Pinchuk |
| 4,649,922 A | 3/1987 | Wiktor |
| 4,655,771 A | 4/1987 | Wallsten |
| 4,665,906 A | 5/1987 | Jervis |
| 4,665,918 A | 5/1987 | Garza et al. |
| 4,681,110 A | 7/1987 | Wiktor |
| 4,719,924 A | 1/1988 | Crittenden et al. |
| 4,728,328 A | 3/1988 | Hughes et al. |
| 4,729,766 A | 3/1988 | Bergentz et al. |
| 4,731,073 A | 3/1988 | Robinson |
| 4,732,152 A | 3/1988 | Wallsten et al. |
| 4,733,665 A | 3/1988 | Palmaz |
| 4,739,762 A | 4/1988 | Palmaz |
| 4,757,827 A | 7/1988 | Buchbinder et al. |
| 4,762,128 A | 8/1988 | Rosenbluth |
| 4,768,507 A | 9/1988 | Fischell et al. |
| 4,772,264 A | 9/1988 | Cragg |
| 4,776,337 A | 10/1988 | Palmaz |
| 4,787,899 A | 11/1988 | Lazarus |
| 4,793,348 A | 12/1988 | Palmaz |
| 4,800,882 A | 1/1989 | Gianturco |
| 4,813,434 A | 3/1989 | Buchbinder et al. |
| 4,815,478 A | 3/1989 | Buchbinder et al. |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,856,516 A | 8/1989 | Hillstead |
| 4,867,173 A | 9/1989 | Leoni |
| 4,872,455 A | 10/1989 | Pinchuk et al. |
| 4,872,874 A | 10/1989 | Taheri |
| 4,878,906 A | 11/1989 | Lindemann et al. |
| 4,886,062 A | 12/1989 | Wiktor |
| 4,886,065 A | 12/1989 | Collins, Jr. |
| 4,898,577 A | 2/1990 | Badger et al. |
| 4,913,141 A | 4/1990 | Hillstead |
| 4,913,701 A | 4/1990 | Tower |
| 4,922,905 A | 5/1990 | Strecker |
| 4,923,464 A | 5/1990 | DiPisa, Jr. |
| 4,938,220 A | 7/1990 | Mueller, Jr. |
| 4,950,227 A | 8/1990 | Savin et al. |
| 4,954,126 A | 9/1990 | Wallsten |
| 4,969,458 A | 11/1990 | Wiktor |
| 4,969,890 A | 11/1990 | Sugita et al. |
| 4,990,151 A | 2/1991 | Wallsten |
| 4,994,071 A | 2/1991 | MacGregor |
| 5,015,253 A | 5/1991 | MacGregor |
| 5,019,085 A | 5/1991 | Hillstead |
| 5,019,090 A | 5/1991 | Pinchuk |
| 5,035,706 A | 7/1991 | Giantureo et al. |
| 5,037,392 A | 8/1991 | Hillstead |
| 5,037,427 A | 8/1991 | Harada et al. |
| 5,041,126 A | 8/1991 | Gianturco |
| 5,042,707 A | 8/1991 | Taheri |
| 5,047,050 A | 9/1991 | Arpesani |
| 5,057,092 A | 10/1991 | Webster, Jr. |
| 5,061,275 A | 10/1991 | Wallsten et al. |
| 5,064,435 A | 11/1991 | Porter |
| 5,067,957 A | 11/1991 | Jervis |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,085,635 A | 2/1992 | Cragg |
| 5,089,005 A | 2/1992 | Harada |
| 5,092,877 A | 3/1992 | Pinchuk |
| 5,098,440 A | 3/1992 | Hillstead |
| 5,102,417 A | 4/1992 | Palmaz |
| 5,104,399 A | 4/1992 | Lazarus |
| 5,104,404 A | 4/1992 | Wolff |
| 5,108,416 A | 4/1992 | Ryan et al. |
| 5,116,318 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,147,370 A | 9/1992 | McNamara et al. |
| 5,151,105 A | 9/1992 | Kwan-Gett |
| 5,158,548 A | 10/1992 | Lau et al. |
| 5,161,547 A | 11/1992 | Tower |
| 5,163,958 A | 11/1992 | Pinchuk |
| 5,178,630 A | 1/1993 | Schmitt |
| 5,183,085 A | 2/1993 | Timmermans |
| 5,190,058 A | 3/1993 | Jones et al. |
| 5,190,546 A | 3/1993 | Jervis |
| 5,192,297 A | 3/1993 | Hull |
| 5,192,307 A | 3/1993 | Wall |
| 5,195,984 A | 3/1993 | Schatz |
| 5,201,757 A | 4/1993 | Heyn et al. |
| 5,201,901 A | 4/1993 | Harada et al. |
| 5,207,695 A | 5/1993 | Trout, III |
| 5,211,658 A | 5/1993 | Clouse |
| 5,219,355 A | 6/1993 | Parodi et al. |
| 5,235,446 A | 8/1993 | Majima |
| 5,236,446 A | 8/1993 | Dumon |
| 5,236,447 A | 8/1993 | Kubo et al. |
| 5,242,399 A | 9/1993 | Lau et al. |
| 5,246,445 A | 9/1993 | Yachia et al. |
| 5,246,452 A | 9/1993 | Sinnott |
| 5,266,073 A | 11/1993 | Wall |
| 5,269,757 A | 12/1993 | Fagan et al. |
| 5,272,971 A | 12/1993 | Fredericks |
| 5,275,622 A | 1/1994 | Lazarus et al. |
| 5,282,823 A | 2/1994 | Schwartz et al. |
| 5,282,824 A | 2/1994 | Gianturco |
| 5,282,860 A | 2/1994 | Matsuno et al. |
| 5,290,305 A | 3/1994 | Inoue |
| 5,292,331 A | 3/1994 | Boneau |
| 5,304,200 A | 4/1994 | Spaulding |
| 5,314,472 A | 5/1994 | Fontaine |
| 5,316,023 A | 5/1994 | Palmaz et al. |
| 5,330,482 A | 7/1994 | Gibbs et al. |
| 5,330,500 A | 7/1994 | Song |
| 5,330,528 A | 7/1994 | Lazim |
| 5,336,164 A | 8/1994 | Snider et al. |
| 5,342,371 A | 8/1994 | Welter et al. |
| 5,342,387 A | 8/1994 | Summers |
| 5,344,425 A | 9/1994 | Sawyer |
| 5,344,426 A | 9/1994 | Lau et al. |
| 5,354,308 A | 10/1994 | Simon et al. |
| 5,354,309 A | 10/1994 | Schnepp-Pesch et al. |
| 5,356,423 A | 10/1994 | Tihon et al. |
| 5,356,433 A | 10/1994 | Rowland et al. |
| 5,360,443 A * | 11/1994 | Barone et al. ................. 623/1.13 |
| 5,365,943 A | 11/1994 | Jansen |
| 5,366,504 A | 11/1994 | Andersen et al. |
| 5,370,618 A | 12/1994 | Leonhardt |
| 5,370,683 A | 12/1994 | Fontaine |
| 5,375,612 A | 12/1994 | Cottencean et al. |
| 5,382,261 A | 1/1995 | Palmaz |
| 5,383,892 A | 1/1995 | Cardon et al. |
| 5,383,926 A | 1/1995 | Lock et al. |
| 5,383,928 A | 1/1995 | Scott et al. |
| 5,385,152 A | 1/1995 | Abele et al. |
| 5,387,235 A | 2/1995 | Chuter |
| 5,389,106 A | 2/1995 | Tower |
| 5,392,778 A | 2/1995 | Horzewski |
| 5,397,345 A | 3/1995 | Lazarus |
| 5,403,341 A | 4/1995 | Solar |
| 5,405,377 A | 4/1995 | Cragg |
| 5,409,019 A | 4/1995 | Wilk |
| 5,413,597 A | 5/1995 | Krajicek |
| 5,415,664 A | 5/1995 | Pinchuk |
| 5,429,144 A | 7/1995 | Wilk |
| 5,433,200 A | 7/1995 | Fleischhacker, Jr. |
| 5,433,723 A | 7/1995 | Lindenberg et al. |
| 5,443,496 A | 8/1995 | Schwartz et al. |
| 5,443,497 A | 8/1995 | Venbrux |
| 5,443,498 A | 8/1995 | Fontaine |
| 5,448,993 A | 9/1995 | Lynch et al. |
| 5,456,713 A | 10/1995 | Chuter |
| 5,464,449 A | 11/1995 | Ryan et al. |
| 5,464,450 A | 11/1995 | Buscemi et al. |
| 5,478,349 A | 12/1995 | Nicholas |

| | | | |
|---|---|---|---|
| 5,480,382 A | 1/1996 | Hammerslag et al. |
| 5,480,423 A | 1/1996 | Ravenscroft et al. |
| 5,484,444 A | 1/1996 | Braunschweiler et al. |
| 5,489,295 A | 2/1996 | Piplani et al. |
| 5,496,344 A | 3/1996 | Kanesaka et al. |
| 5,507,767 A | 4/1996 | Maeda et al. |
| 5,507,768 A | 4/1996 | Lau et al. |
| 5,507,769 A | 4/1996 | Marin et al. |
| 5,507,771 A | 4/1996 | Gianturco |
| 5,522,880 A | 6/1996 | Barone et al. |
| 5,522,882 A | 6/1996 | Gaterud et al. |
| 5,562,678 A | 10/1996 | Booker |
| 5,562,724 A | 10/1996 | Vorwerk et al. |
| 5,562,726 A * | 10/1996 | Chuter ............... 623/1.35 |
| 5,562,727 A | 10/1996 | Turk et al. |
| 5,562,728 A | 10/1996 | Lazarus et al. |
| 5,571,170 A | 11/1996 | Palmaz et al. |
| 5,571,173 A | 11/1996 | Parodi |
| 5,575,817 A | 11/1996 | Martin |
| 5,578,071 A | 11/1996 | Parodi |
| 5,591,195 A | 1/1997 | Taheri et al. |
| 5,597,378 A | 1/1997 | Jervis |
| 5,607,444 A | 3/1997 | Lam |
| 5,609,605 A | 3/1997 | Marshall et al. |
| 5,609,627 A | 3/1997 | Goicoechea et al. |
| 5,613,980 A | 3/1997 | Chauhan |
| 5,617,878 A | 4/1997 | Taheri |
| 5,632,763 A | 5/1997 | Glastra |
| 5,632,772 A | 5/1997 | Alcime et al. |
| 5,634,475 A | 6/1997 | Wolvek |
| 5,639,278 A | 6/1997 | Dereume et al. |
| 5,653,743 A | 8/1997 | Martin |
| 5,662,700 A | 9/1997 | Lazarus |
| 5,669,936 A | 9/1997 | Lazarus |
| 5,676,696 A | 10/1997 | Marcade |
| 5,676,697 A | 10/1997 | McDonald |
| 5,683,449 A | 11/1997 | Marcade |
| 5,683,450 A | 11/1997 | Goicoechea et al. |
| 5,683,451 A | 11/1997 | Lenker et al. |
| 5,683,453 A | 11/1997 | Palmaz |
| 5,687,723 A | 11/1997 | Avitall |
| 5,693,029 A | 12/1997 | Leonhardt |
| 5,693,083 A | 12/1997 | Baker et al. |
| 5,693,086 A | 12/1997 | Goicoechea et al. |
| 5,709,713 A | 1/1998 | Evans et al. |
| 5,713,913 A | 2/1998 | Lary et al. |
| 5,713,917 A | 2/1998 | Leonhardt et al. |
| 5,716,365 A | 2/1998 | Goicoechea et al. |
| 5,718,724 A | 2/1998 | Goicoechea et al. |
| 5,733,303 A | 3/1998 | Israel et al. |
| 5,741,325 A * | 4/1998 | Chaikof et al. ............... 623/1.35 |
| 5,752,522 A | 5/1998 | Murphy |
| 5,782,904 A | 7/1998 | White et al. |
| 5,788,668 A | 8/1998 | Leonhardt |
| 5,797,949 A | 8/1998 | Parodi |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,055 A | 10/1998 | Spiridigliozzi et al. |
| 5,851,210 A | 12/1998 | Torossian |
| 5,860,923 A | 1/1999 | Lenker et al. |
| 5,871,536 A | 2/1999 | Lazarus |
| 5,938,696 A | 8/1999 | Goicoechea et al. |
| 6,024,763 A | 2/2000 | Lenker et al. |
| 6,045,557 A | 4/2000 | White et al. |
| 6,126,685 A | 10/2000 | Lenker et al. |
| 6,165,213 A | 12/2000 | Goicoechea et al. |
| 6,302,906 B1 | 10/2001 | Goicoechea et al. |
| 6,379,372 B1 | 4/2002 | Dehdashtian et al. |
| 6,554,798 B1 | 4/2003 | Mann et al. |
| 6,565,596 B1 | 5/2003 | White et al. |
| 6,582,458 B1 | 6/2003 | White et al. |
| 6,613,073 B1 | 9/2003 | White et al. |

FOREIGN PATENT DOCUMENTS

| | | | |
|---|---|---|---|
| AU | A-32951/95 | 1/1996 |
| CA | 2079944 | 4/1993 |
| DE | 1 766 921 | 1/1970 |
| DE | 28 05 749 A1 | 2/1977 |
| DE | 3918736 | 12/1990 |
| DE | 4219949 | 12/1993 |
| DE | 9319267.30 | 2/1994 |
| EP | 0145166 A2 | 6/1985 |
| EP | 0145166 A3 | 6/1985 |
| EP | 0 183 372 | 4/1986 |
| EP | 0274846 A1 | 7/1988 |
| EP | 0 335 341 | 4/1989 |
| EP | 0364420 A1 | 4/1990 |
| EP | 0364787 A1 | 4/1990 |
| EP | 0 423 916 | 4/1991 |
| EP | 0 421 729 A2 | 10/1991 |
| EP | 461791 A1 | 12/1991 |
| EP | 0464755 A1 | 1/1992 |
| EP | 0466518 A2 | 1/1992 |
| EP | 466518 A3 | 1/1992 |
| EP | 0 472 731 A1 | 3/1992 |
| EP | 0479557 A1 | 4/1992 |
| EP | 0480667 A1 | 4/1992 |
| EP | 481365 A | 4/1992 |
| EP | 0505686 A1 | 9/1992 |
| EP | 508473 A2 | 10/1992 |
| EP | 0518704 A1 | 12/1992 |
| EP | 0518839 A2 | 12/1992 |
| EP | 0518839 A3 | 12/1992 |
| EP | 0533511 A1 | 3/1993 |
| EP | 0 539 237 | 4/1993 |
| EP | 536610 A1 | 4/1993 |
| EP | 540290 A2 | 5/1993 |
| EP | 0540290 A2 | 5/1993 |
| EP | 0540290 A3 | 5/1993 |
| EP | 0 551 179 | 7/1993 |
| EP | 0556850 | 8/1993 |
| EP | 556850 A1 | 8/1993 |
| EP | 0 565 251 A1 | 10/1993 |
| EP | 0 566 245 A1 | 10/1993 |
| EP | 0 541 443 A1 | 12/1993 |
| EP | 575719 A1 | 12/1993 |
| EP | 0 579 523 | 1/1994 |
| EP | 0 596 145 | 5/1994 |
| EP | 603959 A1 | 6/1994 |
| EP | 0 621 016 | 10/1994 |
| EP | 0657147 A2 | 6/1995 |
| EP | 0657147 A3 | 6/1995 |
| EP | 0 656 198 A2 | 7/1995 |
| EP | 0 684 022 | 11/1995 |
| EP | 0 686 379 A2 | 12/1995 |
| EP | 0 783 874 B1 | 7/1997 |
| EP | 0 792 627 B1 | 9/1997 |
| FR | 2 678 508 | 1/1993 |
| FR | 2678508 | * 1/1993 ............... 623/1 |
| FR | 2 714 816 | 7/1995 |
| GB | 2 189 150 A | 10/1987 |
| JP | 05-76603 | 3/1993 |
| JP | 6-197985 | 7/1994 |
| SU | 1217402 | 3/1986 |
| SU | 1318235 A1 | 6/1987 |
| SU | 1457921 A1 | 2/1989 |
| SU | 1697787 | 12/1991 |
| WO | WO 80/02641 | 12/1980 |
| WO | WO 83/00997 | 3/1983 |
| WO | WO 88/00813 | 2/1988 |
| WO | WO 89/01320 | 2/1989 |
| WO | WO89/08433 | 9/1989 |
| WO | WO 90/04982 | 5/1990 |
| WO | WO91/07928 | 6/1991 |
| WO | WO 91/12047 | 8/1991 |
| WO | WO92/00043 | 1/1992 |
| WO | WO 92/06734 | 4/1992 |
| WO | WO 93/13825 | 7/1993 |
| WO | WO 93/15661 | 8/1993 |
| WO | WO93/17636 | 9/1993 |
| WO | WO 93/19804 | 10/1993 |
| WO | WO94/06372 | 3/1994 |
| WO | WO 94/12136 | 6/1994 |
| WO | WO 94/17754 | 8/1994 |
| WO | WO 94/24961 | 11/1994 |
| WO | WO 95/01761 | 1/1995 |

| | | |
|---|---|---|
| WO | WO 95/05207 | 2/1995 |
| WO | WO95/08966 | 4/1995 |
| WO | WO 95/16406 | 6/1995 |
| WO | WO 95/21592 | 8/1995 |
| WO | WO 95/26695 | 10/1995 |
| WO | WO95/29725 | 11/1995 |
| WO | WO 96/10375 | 4/1996 |
| WO | WO 96/11648 | 4/1996 |
| WO | WO96/13228 | 5/1996 |
| WO | WO96/18361 | 6/1996 |
| WO | WO 96/28116 | 9/1996 |
| WO | WO97/03624 | 2/1997 |
| WO | WO 97/16219 | 5/1997 |

OTHER PUBLICATIONS

Brochure—*"Bypass Grafting Without Surgery"*, by Minimally Invasive Technologies, a.k.a. MinTec, Freeport, Grand Bahama, 6 pages, undated.
Brochure—*"Micro Stent"*, by Applied Vascular Engineering, Inc., Santa Rosa, California, 2 pages, Oct. 1994.
Wilson, G. White, et al., *Straight Segment Versus Bifurcation Grafts for Repair of Abdominal Aortic Aneurysm*, Cardiovascular Surgery 1:23-26 (1), Feb. 1993.
May, James, et al., *Endoluminal Repair of Abdominal Aortic Aneurysms*, Med. J. Aust 161:541-543, Nov. 7, 1994.
May, James, et al., *Endoluminal Grafting of Abdominal Aortic Aneurysms: Causes of Failure and Their Prevention*, J. Endovasc. Surg. 1:44-52 (1994).
White, Geoffrey H. et al., *A New Nonstented Balloon-Expandable Graft for Straight or Bifurcated Endoluminal Bypass*, J. Endovasc. Surg. 1:16-24 (1994).
Chuter, T. A. M., et al., *Bifurcated Stent-Grafts for Endovascular Repair of Abdominal Aortic Aneurysm*Surg. Endosc 8:800-802 (1994).
Chuter, T. A. M., et al., *Transfemoral Insertion of a Bifurcated Endovascular Graft for Aortic Aneurysm Repair: The First 22 Patients*, Cardiovascular Surgery 3: 121-128 (2) Apr. 1995.
May, James, et al., *A Prospective Study of Changes in Morphology and Dimensions of Abdominal Aoritic Aneurysms Following Endoluminal Repair: A Preliminary Report*, J. Endovasc. Surg. 2:343-347 (1995).
Declaration of Geoffrey H. White dated Feb. 18, 2000, Opposition EP 0686379.
Declaration of Geoffrey H. White dated Apr. 24, 2001, Opposition EP 0686379.
Declaration of Ian L. Gordon dated Jun. 17, 2000, Opposition EP 0686379.
Declaration of W. Davis, M.D. dated Feb. 28, 2000, Opposition EP 0686379.
White, Geoffrey H. et al., Australia Provisional Patent Application PM 1537, Intraluminal Graft, Sep. 1993.
Declaration of Edward B. Diethrich dated Mar. 8, 2002, Oppositions EP-0792627 and EP 0686379.
Declaration of Geoffrey H. White dated Nov. 22, 2002, Opposition EP 0792627.
Declaration of Timothy J. McGahan dated Nov. 29, 2002, Opposition EP 0792627.
Declaration of Mark Dehdashtian dated Jun. 16, 2000, Opposition EP 0792627.
Complaint for Patent Infringement and Demand for Jury Trial in *Edward Lifesciences LLC et al v. Medtronic, Inc.* et al, Civil Action No. 03-3817, U.S. District Court for the Northern District of California, Aug. 15, 2003.
First Amended Complaint for Patent Infringement and Demand for Jury Trial in *Edward Lifesciences LLC et al v. Medtronic, Inc.* et al, Civil Action No. 03-3817, U.S. District Court for the Northern District of California, Sep. 2, 2003.
Defendant W.L. Gore & Associates, Inc.'s. Answer, Counterclaims and Demand for Jury Trial in *Edward Lifesciences LLC et al v. Medtronic, Inc.* et al, Civil Action No. 03-3817, U.S. District Court for the Northern District of California, Oct. 8, 2003.
Medtronic, Inc. and Medtronic Vascular Inc.'s Answer to the First Amended Complaint; and Counterclaims for Declaratory Judgment of Patent Invalidity, Non-Infringement and Unenforceability in *Edward Lifesciences LLC et al v. Medtronic, Inc. et al*, Civil Action No. 03-3817, U.S. District Court for the Northern District of California, Oct. 8, 2003.
Answer and Counterclaims of Defendant Cook Incorporated in *Edward Lifesciences LLC et al v. Medtronic, Inc. et al*, Civil Action No. 03-3817, U.S. District Court for the Northern District of California, Oct. 20, 2003.
Defendant W.L. Gore & Associates, Inc.'s Preliminary Invalidity Contentions in *Edward Lifesciences LLC et al v. Medtronic, Inc. et al*, Civil Action No. 03-3817, U.S. District Court for the Northern District of California, Mar. 18, 2004.
Medtronic, Inc. and Medtronic Vascular, Inc.'s Preliminary Invalidity Contentions in *Edward Lifesciences LLC et al v. Medtronic, Inc. et al*, Civil Action No. 03-3817, U.S. District Court for the Northern District of California, Mar. 18, 2004.
Preliminary Invalidity Contentions of Cook Incorporated in *Edward Lifesciences LLC et al v. Medtronic, Inc. et al*, Civil Action No. 03-3817, U.S. District Court for the Northern District of California, Mar. 18, 2004.
Medtronic, Inc.'s Complaint Against Geoffrey White for Breach of Contract in *Medtronic, Inc. v. Geoffrey White*, Civil Action No. Apr. 2201, U.S. District Court for the Northern District of California, Jun. 4, 2004.
Answer of Dr. Geoffrey H. White in *Medtronic, Inc. v. Geoffrey White*, Civil Action No. Apr. 2201, U.S. District Court for the Northern District of California, Jun. 24, 2004.
Complaint for Intervention in *Medtronic, Inc. v. Geoffrey White*, Civil Action No. 04-2201, U.S. District Court for the Northern District of California, Nov. 18, 2004.
Expert Report of Dr. Hugh G. Beebe in *Medtronic, Inc. v. Geoffrey White*, Civil Action No. 04-2201, U.S. District Court for the Northern District of California, Sep. 26, 2005 [Redacted, Non-Confidential].
Declaration of Alexander Balko, M.D. in Support of Defendants' Motion for Summary Judgment as to Invalidity under Section 102 of the Patent Act.
The Party White et al.'s 37 CFR 1.608(b) Declaration of Geoffrey H. White, M.D.
Declaration of Dr. Geoffrey H. White in Support of Defendant's Motion for Summary Judgment of the Issue of Ownership of the Patents in Suit.
Apr. 22, 1988 Consulting Agreement Medtronic and Dr. White.
Jul. 21, 1989 Consulting Agreement Medtronic and Dr. White.
Order re Cross-Motions for Summary Judgment; Order Denying Dr. White's Motion to Strike; Order Imposing Sanctions for Violating Rule 15.
The Party White et al.'s 37 CFR 1.608(b) Declaration of Mark Desdashtian.
White et al's. Second 37 CFR 1.608 Declaration of Ian Gordon.
*The American Heritage Dictionary*, copyright 1978, pp. 356, 373.
*Webster's Third New International Dictionary*, copyright 1971, selected pages (no. nos.).
*Webster's New Twentieth Century Dictionary*, copyright 1972, selected pages (no. nos.).
*Webster's Third New International Dictionary*, copyright 1986, selected pages (no. nos.).
Declaration of Geoffrey H. White, M.D. in Support of Plaintiffs' Response to Medtronic's Motion to Dismiss.
"*Endoluminal Vascular Prosthesis*,".
International Society for Cardiovascular Surgery, 24th World Congress, Sep. 12-17, 1999, Call for Abstracts.
International Society for Cardiovascular Surgery, 24th World Congress, Sep. 12-17, 1999, Preliminary Information.
International Society for Cardiovascular Surgery, 24th World Congress, Sep. 12-17, 1999, Physician Meeting Registration Form.
The Phoenician Resort, 1999.
*German Patent Application*, Date of application: Dec. 15, 1993, Title of the object: Aortic endoprosthesis.
*The Gray Sheet®*, Jul. 1998.
*CardioVascular and Interventional Radiology*, 1992, Do-dai-Do, et al, "A Comparison Study of Self-Expandable Stents vs Balloon Angioplasty Alone in Femoropopliteal Artery Occlusions".

*CardioVascular and Interventional Radiology*, 1992, D. Liermann et al, "The Strecker Stent: Indications and Results in Iliac and Femoropopliteal Arteries".
*Journal of Vascular Surgery*, 1990, Michael S. Trent, MD, et al, "A balloon-expandable intravascular stent for obliterating experimental aortic dissection".
*Journal of Vascular Surgery*, 1986, C. P. Shearman, F.R.C.S., et al, "A clinical method for the detection of arteriovenous fistulas during in-situ great saphenous vein bypass".
*110th Annual Meeting of the American Surgical Association*, Apr. 5-7, 1990, Rodney A. White, M.D., et al, "A Clinical Trial of Laser Thermal Angioplasty in Patients With Advanced Peripheral Vascular Disease".
*ASAIO Journal*, 1993, G. J. Wilson et al, "A Complaint Corethane/Dacron Composite Vascular Prosthesis Comparison with 4-mm ePTFE Grafts in a Canine Model".
*Journal of Endovascular Surgery*, 1998, Ralph I. Rückert, MD, et al, "A Method for Adjusting a Malpositioned Bifurcated Aortic Endograft".
*Journal of Endovascular Therapy*, 2000, Robin H. Heijmen, MD, PhD, et al, "A Narrow-Waisted Abdominal Aortic Aneurysm Complicating Endovascular Repair".
*Journal of Endovascular Therapy*, 2000, Wesley S. Moore, MD, "A Narrow-Waisted Aortic Aneurysm Need Not Hinder Endovascular Graft Repair".
*JACC*, Mar. 15, 1992, Christopher J. White, MD, FACC, et al, "A New Balloon-Expandable Tantalum Coil Stent: Angiographic Patency and Histologic Findings in an Atherogenic Swine Model".
*The Journal of Thoracic and Cardiovascular Surgery*, Aug. 1987, William H. Heydorn, MD, Colonel, MC, USA, et al, "A new look at pericardial substitutes".
*Proceedings of the First International Conference on Shape Memory and Superelastic Technologies*, 1994, J. E. Bramfitt et al, "A Novel Heat Activated Recoverable Temporary Stent (Harts System)".
*Circulation*, 1995, Carlos E. Ruiz, MD, PhD, et al, "A Novel Method for Treatment of Abdominal Aortic Aneurysms Using Percutaneous Implantation of a Newly Designed Endovascular Device".
*Journal of Endovascular Surgery*, 1995, James May, MS, FRACS, FACS, et al, "A Prospective Study of Changes in Morphology and Dimensions of Abdominal Aortic Aneurysms Following Endoluminal Repair: A Preliminary Report".
*Journal of Endovascular Surgery*, 1998, A. Ballaro, et al, "A Seasonal Variation in the Incidence of Ruptured Abdominal Aortic Aneurysms".
*Vascular Surgery Department, Royal Perth Hospital*, 1996, M. K. Gordon, et al, "A Self-Expanding Endoluminal Graft for Treatment of Aneurysms: Results Through the Development Phase".
*Journal of Vascular and Interventional Radiology*, May-Jun. 1997, Michael J. Hallisey, MD, "A Transluminally Created Abdominal Aortic Aneurysm Model".
*Circulation*, Feb. 1989, Richard A. Schatz, MD, "A View of Vascular Stents".
*"The Gray Sheet"* May 2001, "AAA Endovascular Graft Patient Imaging Follow-Up Recommended by FDA".
*In Vivo: The Business and Medicine Report*, 1998, Stephen Levin, "AAA Surgery: Bet Early and Often".
*Cardiovascular Radiology*, Mar. 1995, Richard H. Cohan, MD, et al, "Abdominal Aortic Aneurysm: CT Evaluation of Renal Artery Involvement".
*Journal of Endovascular Surgery*, 1999, Timothy Resch, MD, et al, "Abdominal Aortic Aneurysm Morphology in Candidates for Endovascular Repair Evaluated With Spiral Computed Tomography and Digital Subtraction Angiography".
*Stent-Grafting for Abdominal Aortic Aneurysms*, 1998, Ulrich Blum, MD, et al, "Abdominal Aortic Aneurysm Repair Using the Meadox/Vanguard Prosthesis: Indications, Implantation Technique, and Results".
*Talent Stent Graft*, 1998, Lindsay Machan, MD, et al, "Abdominal Aortic Aneurysm Repair Using the World Medical Talent Prosthesis".
*Journal of Endovascular Surgery*, 2000, Rodney A. White, MD, et al, "Abdominal Aortic Aneurysm Rupture Following Endoluminal Graft Development: Report of a Predictable Event".

*Remon Medical Technologies, Ltd.*, Mar. 2000, "AAA Monitoring System".
*Journal of Endovascular Surgery*, 1997, Krassi Ivancev, MD, et al, "Abdominal Aortic Aneurysms: Experience With Ivancev-Malmö Endovascular System for Aortomonoiliac Stent-Grafts".
*Interventional Radiology*, Jan. 1996, Ulrich Blum, MD, et al, "Abdominal Aortic Aneurysms: Preliminary Technical and Clinical Results with Transfemoral Placement of Endovascular Self-expanding Stent-Grafts".
*Proceedings of the Second International Conference on Shape Memory and Superelastic Technologies*, 1997, Richard Glenn et al, "Accelerated Pulsitile Fatigue Testing of Ni-Ti Coronary Stents".
*Journal of Endovascular Surgery*, 1999, Claudio Schönholz, MD, et al, "Acute Rupture of an Aortic False Aneurysm Treated With a Stent-Graft".
*Journal of Vascular Surgery*, Oct. 2000, Laura A. Karch, MD, et al, "Adverse consequences of internal iliac artery occlusion during endovascular repair of abdominal aortic aneurysms".
*Br. J. Surg.*, 1990, May, K. G. Burnand, "Aetiology of Venous Ulceration".
*Arizona Heart Foundation*, 1993, [brochure] "Alternatives to Surgery".
*Seminars in Vascular Surgery*, Dec. 1997, Takao Ohki, et al, "Varying Strategies and Devices for Endovascular Repair of Abdominal Aortic Aneurysms".
*Journal of Vascular Surgery*, 1999, Gerald S. Treiman, MD, et al, "An assessment of the current applicability of the EVT endovascular graft for treatment of patients with an infrarenal abdominal aortic aneurysm".
*Journal of Vascular Surgery*, Jul. 1988, Masaru Matsumae, MD, et al, "An experimental study of a new sutureless intraluminal graft with an elastic ring that can attach itself to the vessel wall".
*Aust. N.Z. J. Surg.*, 1992, G. M. McMullin, et al, "An Evaluation of Doppler Ultrasound and Photoplethysmography in the Investigation of Venous Insufficiency".
*Journal of Vascular Surgery*, 2000, Daniel G. Clair, MD, et al, "An evaluation of the costs to health care institutions of endovascular aortic aneurysm repair".
*The Journal of Cardiovascular Surgery*, 1993, E. Tardito, M.D., et al, "Anastomotic disjunction in long-term patent vascular synthetic grafts in Dacron®".
*Journal of Vascular Surgery*, 1988, Gerald S. Treiman, MD, et al, "Anastomotic false aneurysms of the abdominal aorta and the iliac arteries".
*Seminars in Vascular Surgery*, 1989, Geoffrey H. White, et al, "Ancillary Modalities for Endovascular Surgery: Guidance Systems, Vascular Stents, and Methods to Prevent Restenosis".
*Progress in Cardiovascular Diseases*, Jan./Feb. 1992, David A. Kumpe, et al, "Angioplasty/Thrombolytic Treatment of Failing and Failed Hemodialysis Access Sites: Comparison With Surgical Treatment".
*The Surgical Clinics of North America*, Aug. 1992, Geoffrey H. White, MB BS, FRACS, "Angioscopy".
*Current Therapy in Vascular Surgery*, Second Edition, 1991, Rodney. A. White, M.D. et al, "Angioscopy in the Management of Infrainguinal Occlusive Arterial Disease".
*Radiology-JVIR*, 1991, Julio C.. Palmaz, MD, et al, "Aortic Bifurcation Stenosis: Treatment With Intravascular Stents".
*J Endovasc Ther*, 2004, Boonprasit Kritpracha, MD, et al, "Aortic Diameter is an Insensitive Measurement of Early Aneurysm Expansion After Endografting".
*J Endovasc Ther*, 2000, Kimihiko Kichikawa, MD, et al, "Aortic Stent-Grafting With Transrenal Fixation: Use of Newly Designed Spiral Z-Stent Endograft".
*Departments of Surgery, Pathology and Medicine Harbor-UCLA Medical Center, Presented at the 1986 Southern California Vascular Surgical Society Meeting*, Sep. 26-28, 1986, Rodney A. White, M.D., et al, "Aortitis Presenting as Buerger's Disease".
*J Endovasc Surg*, 1997, Hugh G. Beebe, MD, "Imaging Modalities for Aortic Endografting".
*SPIE vol. 712 Lasers in Medicine*, 1986, George Kopchok, et al, "Argon laser vascular welding: The thermal component".

*The American Journal of Surgery*, Aug. 1985, Larry S. Nichter, MD, et al, "Arterialized Venous Perfusion of Composite Tissue".
*Aust. N.Z. Surg.*, 1990, Bo Almgren, et al, "Arteriovenous Fistula Following Transfemoral Angiography".
*Anesthesiology*, 1978, William D. Owens, M.D., et al, "ASA Physical Status Classifications: A Study of Consistency of Ratings".
*Surgery*, Oct. 1981, John P. Harris, M.D., et al, "Assessment of donor limb hemodynamics in femorofemoral bypass for claudication".
*Radiology*, 1986, Julio C. Palmaz, et al, "Atherosclerotic Rabbit Aortas: Expandable Intraluminal Grafting".
*Surgical Rounds*, Jul. 1992, James Robert Wendt, M.D., "Avoiding Serious Complications with Central Venous Access".
*The American Journal of Surgery*, Aug. 1999, Walter E. McGregor, MD, et al, "Awake Aortic Aneurysm Repair in Patients with Severe Pulmonary Disease".
*Circulation*, 1987, Richard A. Schaz, M.D., et al, "Balloon expandable intracoronary stents in the adult dog".
*International Congress VI, Endovascular Interventions*, 1993, Official Program, and: MR Rees, et al, "Treatment of Peripheral Vascular Disease With the Pullback Atherectomy Catheter—Assessment by Intravascular Ultrasound and Angioscopy"; TJ Fogarty, et al, "Continuous Monitoring of the Reperfused Limb via Piezoelectric Measurement of Peripheral Pulse Amplitude"; G White et al, "Experimental Endoluminal Grafts and Coated Stents".
*AJR*, Jun. 1988, Julio C. Palmaz, "Balloon-Expandable Intravascular Stent".
*Journal of Vascular Surgery*, May 2002, Boonprasit Kritpracha, MD, et al, "Bell-bottom aortoiliac endografts: An alternative that preserves pelvic blood flow".
*Presented to the 15th Annual meeting of the Peripheral Vascular Society*, Los Angeles, Jun. 1990, John P. Harris, MS, FRACS, FRCS, FACS, et al, "Bench Repair of Complex Renal Arterial Lesions".
*Seminars in Vascular Surgery*, Jun. 2003, Hugh G. Beebe, "Lessons Learned from Aortic Aneurysm Stent Graft Failure; Observations From Several Perspectives".
*J Endovasc Ther*, 2004, Boonprasit Kritpracha, MD, et al, "Post-Endograft Abdominal Aortic Aneurysm Shrinkage Varies Among Hospitals: Observations From Multicenter Trials".
*Journal of Vascular Surgery*, Jan. 2004, Jeffrey P. Carpenter, MD, "Multicenter pivotal trial results of the Lifepath System for endovascular aortic aneurysm repair".
*BioMaterials & Surgery*, Feb. 1999, magazine.
*J Endovasc Ther*, 2003, Hiranya A. Rajasinghe, MD, et al, "Internal Iliac Artery Occlusion Using a Stent-Graft Tunnel During Endovascular Aneurysm Repair: A New Alternative to Coil Embolization".
*Circulation*, Jul. 25, 2000, Antonio Colombo, MD, et al, "Biodegradable Stents 'Fulfilling the Mission and Stepping Away'".
*Surgery Today*, 1999, Kazuya Akiyama, et al, "Bleeding Through the Fiber Intersticas of a Knitted Dacron Graft 12 Years After Its Implantation: Report of a Case".
*International Endovascular Symposium*, Dec. 5-7, 2002, Book of Proceedings.
*AOL News*; Jul. 1, 1998, "Boston Scientific Announces Acquisition of CardioGene Therapeutics, Inc.".
*Cardiovascular Interventions*, Sep. 1998, "CVI Online".
*J Endovasc Ther*, 2000, Chung K. Shin, MD, et al, "Can Preoperative Spiral CT Scans Alone Determine the Feasability of Endovascular AAA Repair? A Comparison to Angiographic Measurements".
*Canadian Society for Vascular Surgery. 20th Annual Meeting*, Friday, Sep. 25-Sunday, Sep. 27, 1998, Memo, selected abstracts.
*CardioVascular and Interventional Radiology*, 1991, Georg Kuffer, et al, "Percutaneous Reconstruction of the Aortic Bifurcation With Palmaz Stents: Case Report".
*CardioVascular and Interventional Radiology*, 1991, Ducksoo Kim, et al, "Use of a Reperfusion Catheter after Angioplasty Dissection for Salvage of Ischemic Renal Allograft: Case Report".
*CardioVascular and Interventional Radiology*, 1991, Rolf W. Günther, et al, "Minibasket for Percutaneous Embolectomy and Filter Protection Against Distal Embolization: Technical Note".
*Circulation*, Oct. 15, 1996, Shram S Iyer, et al, "Cardiovascular Radiology: Stents and Stent Grafts—Carotid, Subclavian, and Aortic Applications".

*AJR*, Jul. 1992, Richard A. Clugston, et al, "Case Report Atherectomy of the Distal Aorta using a 'Kissing-Balloon' Technique for the Treatment of Blue Toe Syndrome".
*Journal of Vascular and Interventonal Radiology*, 1995, Bryan D. Petersen, MD et al, "Gianturco-Rösch Z Stents in Tracheobronchial stenoses".
*The Journal of Cardiovascular Surgery*, Aug. 1995, M. Tolan, M.D., et al, "Clinical experience with a collagen impregnated woven dacron graft".
*Journal of Cardiac Surgery*, Sep. 1988, Carmine Minale, M.D., et al, "Clinical Experience with Expanded Polytetrafluoroethylene Gore-Tex® Surgical Membrane for Pericardial Closure: A Study of 110 Cases".
*BMJ*, May 2000, C O S Savage, et al, "ABC of arterial and vascular disease Vasculitis".
*The Thoracic and Cardiovascular Surgeon*, Oct. 1987, C. Minale, et al, "Closure of the Pericardium Using Expanded Polytetrafluoroethylene GORE-TEX®—Surgical Membrane: Clinical Experience".
*Thorac.cardiovasc.Surgeon 39* (1991), S. W. Hirt, et al, "Collagen-presealed or Uncoated Aortic Bifurcation Dacron Prostheses: A 5-Year Clinical Follow-Up Study".
*Arch Surg*, Mar. 1987, Edward M. Kwasnik, MD, et al, "Comparative Results of Angioplasty and Aortofemoral Bypass in Patients With Symptomatic Iliac Disease".
*Journal of Vascular Surgery*, Sep. 1999, Lemuel B. Kirby, MD, et al, "Comparison between the transabdominal and retroperitoneal approaches for aortic reconstruction in patients at high risk".
*Journal of Vascular and Interventional Radiology*, Mar.-Apr. 1994, Steven V. Lossef, MD, et al, "Comparison of Mechanical Deformation Properties of Metallic Stents With Use of Stress-Strain Analysis".
*American Heart Journal*, May 1996, Neal A. Scott, MD, PhD, et al, "Comparison of the thrombogenicity of stainless steel and tantalum coronary stents".
*The Society of Thoracic Surgeons*, 1994, Marcela Pekna, MD, PhD, et al, "Complement Activation During Cardiopulmonary Bypass: Effects if Immobilized Heparin".
*Eur J Vasc Endovasc Surg*, 1999, Ph. Cuypers, et al, "Complications in the Endovascular Repair of Abdominal Aortic Aneurysms: a Risk Factor Analysis".
*Journal of Vascular Surgery*, Feb. 2001, Rodney A. White, MD, et al, "Computed tomography assessment of abdominal aortic aneurysm morphology after endograft exclusion".
*Stroke*, Feb. 1996, Hugh G. Beebe, MD, et al, "Concern About Safety of Carotid Angioplasty".
*Start-Up*, May 1996, Wendy Diller, "Coronary Stents: Breaking J&J's Lock on the Market".
*The American Journal of Surgery*, Aug. 1999, Andrew J. Seiwart, MD, et al, "Cost Comparison of Aortic Aneurysm Endograft Exclusion versus Open Surgical Repair".
*J Endovasc Ther*, 2002, Boonprasit Kritpracha, MD, et al, "CT Artifacts of the Proximal Aortic Neck: An Important Problem in Endograft Planning".
*Current Critical Problems in Vascular Surgery*, vol. 2, © 1990, Geoffrey H. White, MD, "How Angioscopy Can Be Helpful to the Vascular Surgeon".
*Interoperative Angioscopy*, 1989, Geoffrey H. White, et al, "Current Role of Intraoperative Angioscopy for Monitoring Peripheral Vascular Surgery".
*Vascular Surgery*, May/Jun. 1998, Samuel S. Ahn, MD, et al, "Current Status of Intraluminal Grafts for Aortic Aneurysms".
*Cardiology Clinics*, Nov. 1994, Ernst-Peter Strecker, MD, et al, "Current Status of the Strecker Stent".
*The New England Journal of Medicine*, Jan. 1997, Calvin B. Ernst, M.D., "Current Therapy for Infrarenal Aortic Aneurysms".
*Current Therapy in Vascular Surgery*, © 1987, Geoffrey H. White, M.D., et al, "Direct Arteriovenous Asastomoses for Angioaccess".
*Surgery*, Dec. 1982, M. Goldman, F.R.C.S., et al, "Dacron arterial grafts: The influence of porosity, velour, and maturity on thrombogenicity".

*J Endovasc Surg*, 1999, M. Elske Sitsen, MD, et al, "Deformation of Self-Expanding Stent-Grafts Complicating Endovascular Peripheral Aneurysm Repair".
*The American Journal of Surgery*, Aug. 1995, Alan B. Lumsden, et al, "Delayed Rupture of Aortic Aneurysms Following Endovascular Stent Grafting".
*Circulation*, Feb. 1999, H. Rousseau, MD, et al, "Delayed Treatment of Traumatic Rupture of the Thoracic Aorta With Endoluminal Covered Stent".
*Proceedings of the Second International Conference on Shape Memory and Superelastic Technologies*, 1997, J.L. Longas, et al, "Design Characteristics and Mechanical Properties of a New Ni-Ti Stent".
*Proceedings of the Second International Conference on Shape Memory and Superelastic Technologis*, 1997, Guo Jinfang, et al, "Designs and Medical Applications of NITI SMA Self-Expanding Stents in China".
*Dis Vanage Health Outcomes*, 1997, Warren E. Todd, et al, "Disease Management: Building a Solid Foundation".
*Vascular Surgery*, Jan./Feb. 1989, Lisbeth Jorgensen, M.D., et al, "Dissecting Aneurysm of Infrarenal Abdominal Aorta—A Case Report".
*Journal of Vascular Surgery*, Dec. 1986, Jonathan D. Beard, F.R.C.S.. et al, "Does the in-situ technique for autologous vein femoropopliteal bypass offer any hemodynamic advantage?"
*Journal of Biomedical Materials Research*, 1989, A. Cigada et al, "Duplex stainless steels for osteosynthesis devices ".
*Surgery*, Mar., 1986, D. Buchbinder, M.D. et al, "Early experience with in-situ saphenous vein bypass for distal arterial reconstruction".
*Journal of Vascular Surgery*, Mar. 2001, Yehuda G. Wolf, MD, et al, "Eccentric stent graft compression: An indicator of insecure proximal fixation of aortic stent graft".
*Aus. N.Z.J. Surgf*1991, G. M. McMullin, et al, "Efficacy of Fibrinolytic Enhancement With Stanozolol in the Treatment of Venous Insufficiency".
*Eighth Annual International Symposium on Vascular Diagnosis and Intervention*, Jan. 28-Feb. 1, 1996, Final Program.
*The Journal of Thoracic and Cardiovascular Surgery*, Sep. 1999, Pasquale Mastroroberto, MD, et al, "Emergency Thoracoabdominal Aortic Aneurysm Repair: Clinical Outcome".
*EndoCardioVascular Multimedia Magazine*, Sep. 1998.
*J Endovasc Surg*, 1997, Hugh G. Beebe, MD, "Endografting in Aortic Trauma: Let's Keep it in Perspective".
*Journal of Endovascular Surgery*, 1995, GJ Becker et al, "Endografts for the Treatment of Aneurysm and Traumatic Vascular Lesions: MVI Experience".
*Journal of Endovascular Surygery*, Jul. 2000, Christopher K. Zarins, et al, "Endoleak as a predictor of outcome after endovascular aneurysm repair: AneuRx multicenter clinical trial".
*Journal of Endovascular Surgery*, Jan. 1998, Reese A. Wain et al, "Endoleaks after endovascular graft treatment of aortic aneurysms: Classification, risk factors and outcome".
*Eur J Vasc Endovasc Surg*, 2000, C.L.H. Chen et al, "Endoleaks Following Conventional Open Abdominal Aortic Aneurysm Repair".
*Journal of Endovascular Surgery*, Aug. 1998, G. W. H. Schurink, MD, et al, "Endoleakage after stent-graft treatment of abdominal aneurysm: Implications on pressure and imaging—an in vitro study".
*3rd Annual Symposium on Endovascular Therapies*, Nov. 26-27, 1993, Secretariat Report.
*Texas Heart Institute Journal*, 1997, Zvonimir. Krajcer, MD, et al, "Endoluminal Exclusion of an Iliac Artery Aneurysm by Wallstent® Endoprothesis and PTFE Vascular Graft".
*Journal of Endovascular Surgery*, 1999, Willem Wisselink, MD, et al, "Endoluminal Repair of Aneurysms Containing Ostia of Essential Branch Arteries: An Experimental Model".
*The New England Journal of Medicine*, Jan. 1997, Ulrich Blum, MD, et al, "Endoluminal Stent-Grafts for Infrarenal Abdominal Aortic Aneurysms".
*Journal of Vascular and Interventional Radiology*, Mar. 1999, Klaus A. Hausegger, MD, et al, "Endoluminal Treatment of Infrarenal Aortic Aneurysms: Clinical Experience with the Talent Stent-Graft System".

Volume 36, 1990, W. Domschke, MD, et al, "Endoscopic implantation of large-bore self-expanding biliary mesh stent".
*Endoscopic intravascular surgery*, Feb. 1990, Geoffrey H. White, MD, et al, "Endoscopic Intravascular Surgery Removes Intraluminal Flaps, Dissections, and Thrombus".
*Arch Surg*, Feb. 1993, Christer Drott, MD, PhD, et al, "Endoscopic Procedures of the Upper-Thoracic Sympathetic Chain".
*J Endovasc Surg*, 1999, Stuart R. Walker, FRCS, et al, "Endovascular AAA Repair: Prevention of Side Branch Endoleaks With Thrombogenic Sponge".
*Eur J Vasc Endovasc Surg*, Oct. 1997, Th. J. Hölzenbein, et al, "Endovascular AAA Treatment: Expensive Prestige or Economic Alternative?".
*Texas Heart Institute Journal*, 2000, Marcus H. Howell, MD, et al, "Endovascular Exclusion of Abdominal Aortic Aneurysms".
*Endovascular Surgery*, Aug. 1993, Harrison M. Lazarus, MD, "Endovascular Grafting for the Treatment of Abdominal Aortic Aneurysms".
*Ann Surg*, May 1996, William H. Edwards, Jr., M.D., et al, "Endovascular Grafting of Abdominal Aortic Aneurysms: A Preliminary Study".
*Eur J Vasc Endovasc Surg*, Jan. 2000, M. Malina, et al, "Endovascular Healing is Inadequate for Fixation of Dacron Stent-Grafts in Human Aortoiliac Vessels".
*Eur J Vasc Endovasc Surg*, 1996, G. H. Ho, et al, "Endovascular and Surgical Techniques Endovascular Remote Endarterectomy in Femoropopliteal Occlusive Disease: One-Year Clinical Experience With the Ring Strip Cutter Device".
*Journal of Vascular Surgery*, Sep. 2000, Yehuda G. Wolf, MD, et al, "Endovascular repair of abdominal aortic aneurysms: Eligibility rate and impact on the rate of open repair".
*JVIR*, Apr. 2000, Thomas J. Franco, MD, et al, "Endovascular Repair of Abdominal Aortic Aneurysm with the Ancure Endograft: CT Follow-Up of Perigraft Flow and Aneurysm Size at 6 Months".
*Journal of Vascular Surgery*, Sep. 1999, David B. Kaplan, MD, "Endovascular repair of abdominal aortic aneurysms in patients with congenital renal vascular anomalies".
*World Journal of Surgery*, 1996, Juan C. Parodi, MD., "Endovascular Repair of Aortic Aneurysms. Arteriovenous Fistulas, and False Aneurysms".
*Ann Thorac Surg*, 1998, Marek Ehrlich, MD, et al, "Endovascular Stent Graft Repair for Aneurysms on the Descending Thoracic Aorta".
*European Journal of Vascular Endovascular Surgery*, May 1993, R. D. Sayers, et al, "Endovascular Stenting of Abdominal Aortic Aneurysms".
*Journal of Vascular Surgery*, 1999, Rodney A. White, MD, et al, "Endovascular interventions training and credentialing for vascular surgeons".
*Journal of Endovascular Surgery*, 1994, Frank J. Criado, MD, et al, "Endovascular Surgery in Daily Practice: A Re-Appraisal".
*Journal of Endovascular Surgery 1998*; H. G. Beebe, MD, "Endovascular Surgery: Issues and Opportunities as We Approach the New Millennium".
*Endovascular Surgery*, Jul. 1992, Samuel S. Ahn, M.D., et al, "Endovascular Surgery for Peripheral Arterial Occlusive Disease".
*EndoCardioVascular WEB Magazine Multimedia Journal of Emerging Endocardiovascular Technologies*, Feb. 2002.
*Endovascular Symposium*, Nov. 25-27, 1993, Registration Brochure.
*Journal of Vascular Surgery*, Jul. 1999, William J. Quinones-Baldrich, MD, et al, "Endovascular, transperitoneal, and retroperitonealabdominalaorticaneurysm repair: Results and costs".
*Journal of Endovascular Surgery*, 2000, Per Birger Lundquist, MD, et al, "Endovascular Treatment of Atherosclerotic Lower Limb Lesions Using a PTFE-Collared Stent-Graft".
*Endovascular Treatment of Iliac Limb Stenoses or Occlusions*, Apr. 2000, Nikhil B. Amesur, MD, et al, "Endovascular Treatment of Iliac Limb Stenoses or Occlusions in 31 Patients Treated with the Ancure Endograft".
*Annals of Vascular Surgery*, 1998, James May, MS, FRACS, FACS, et al, "Endovascular Treatment of Infrarenal Abdominal Aneurysms".
*Endovascular Update*, Jun. 1999.

*Arch Surg*, Sep. 1999, Christian de Virgilio, MD, et al, "Endovascular vs Open Abdominal Aortic Aneurysm Repair".
*Entrepreneur*, Nov. 1996, Roger Longman, "Engineering Medicine: Tom Fogarty & Medical Device Start-Ups".
*Langenscheidts Grossworterbuch*, definition of a word.
*International Vascular Imaging & Intervention, 4th International Congress of Angiography and Vascular Intervention*, Jul. 4-7, 1996, Final program and abstracts.
*American Journal of Radiology*, Oct. 1986, Julio C. Palmaz, et al, "Expandable Intrahepatic Portacaval Shunt Stents: Early Experience in the Dog".
*Radiology*, 1985, Julio C. Palmaz, et al, "Expandable Intraluminal Graft: A Preliminary Study".
*The American Journal of Surgery*, Dec. 1989, Geoffrey H. White, MD, et al, "Experimental and Clinical Applications of Angioscopic Guidance for Laser Angioplasty".
*Journal of Endovascular Surgery*, 1997, Timothy A. M. Chuter, MD, et al, "European Experience With a System for Bifurcated Stent-Graft Insertion".
*Published Journal of Endovascular Surgery*, 1997; Timothy AM Chuter, "European Experience With the Chuter Bifurcated Endograft".
*International Society for Endovascular Surgery*, Jun. 1996 European Summer Symposium, Program and Compilation of abstracts.
*Journal of Cardiovascular Surgery*, 1991, Lawrence M. Hanrahan, MD, et al, "Evaluation of the perforating veins of the lower extremity using high resolution duplex imaging".
*The Society of Thoracic Surgeons*, 1997, Thomas A. Orszulak, MD, et al, "Event Status of the Starr-Edwards Aortic Valve to 20 Years: A Benchmark for Comparison".
*Eur Heart*, 1999, J.T. Powell, "Evidence against prophylactic repair of small, asymptomatic abdominal aortic aneurysms".
*Disease State Management*, 1997, John H. Eichert et al, "Factors Affecting the Success of Disease Management".
*Radiology*, Jul. 1988, Charles R. Meyer, PhD, et al, "Feasibility of High-Resolution, Intravascular Ultrasonic Imaging Catheters".
*Federal Register*, Jun. 23, 1978, Sherwin Gardner, Acting Commissioner of Food and Drugs, "Ethylene Oxide, Ethylene Chlorohydrin, and Ethylene Glycol Proposed Maximum Residue Limits and Maximum Levels of Exposure".
*Federal Register*, Aug. 16, 1993, Michael R. Taylor, Deputy Commissioner for Policy, "Medical Devices; Device Tracking; Opportunity for Comments".
*Surgery*, Jan. 1968, Jack A. Cannon, M.D., et al, "Femoral Popliteal Endarterectomy in the Treatment of Obliterative Atherosclerotic Disease".
*Surgery*, 1990, P. R. Meech, "Femoral Neuropathy Following Renal Transplantation".
*Femoral Vascular Injury*, Nov. 1991, Geoffrey H. White, "Femoral Vascular Injury During Hernia Repair".
*Br. J. Surg.*, 1982, M. Goldman, et al, "Femoropopliteal bypass grafts—an isotope technique allowing in vivo comparison of thrombogenicity".
*Fifth Annual International Symposium on Vascular Diagnosis and Intervention*, Jan. 1993, Goetz M. Richter, M.D., et al, "Results of Randomized Trial of PTA vs. Primary Stenting".
*Journal of Endovascular Therapy*, 2000, Robert Guidoin, PhD, et al, "First-Generation Aortic Endografts: Analysis of Explanted Stentor Devices from the Eurostar Registry".
*Radiology*, 1990, Klemens H. Barth, MD, et al, "Flexible Tantalum Stents Implanted in Aortas and Iliac Arteries: Effects in Normal Canines".
*Journal of Endovascular Surgery*, 1999; Hirofumi Midorikawa, MD, PhD, et al, "Graft-Wall Endoleak 18 Months After Successful Endoluminal AAA Repair".
*The Lancet*, Nov. 1998, Dr. J F Forbes, "Health service costs and quality of life for early elective surgery or ultrasonographic surveillance for small abdominal aortic aneurysms".
*44th Annual Meeting of the Scandinavian Association for Thoracic Surgery*, 1995, O. Moen, et al, "Heparin Coated Surfaces Reduce Complement and Granulocyte Activation During CPB-A Comparison of Bentley Duraflo II and the Carmeda BioActive Surface (CBAS)".
*The Society of Thoracic Surgeons*, 1995, E. Ovrum, et al, "High and Low Heparin Dose With Heparin-Coated Cardioupulmonary Bypass: Activation of Complement and Granulocytes".
*AATS Presentations*, 1995, RC Gorman, et al, "Surface—Bound Heparin Fails to Reduce Thrombin Formation During Clinical Cariopulmonary Bypass".
*Journal of Vascular Surgery*, Feb. 2000, W. Charles Sternbergh III, MD, et al, "Hospital cost of endovascular versus open repair of abdominal aortic aneurysms: a multicenter study".
*Br. J. Surg.*, 1983, M. Goldman, et al, "Human umbilical vein and polytetrafluorethylene arterial grafts compared in an artificial circulation".
*Arch Surg*, Nov. 1978, P. Flanigan, MD, et al, "Hemodynamic and Angiographic Guidelines in Selection of Patients for Femorofemoral Bypass".
*Journal of Vascular Surgery*, Aug. 2001, Jon S. Matsumura, MD, et al, "Identification and implications of transgraft microleaks after endovascular repair of aortic aneurysms".
*Radiology*, 1989, Rolf W. Gunther, MD, et al, "Iliac and Femoral Artery Stenoses and Occlusions: Treatment with Intravascular Stents".
*Journal of Endovascular Surgery*, 1999, Frank J. Criado, MD, "Iliac Bifrucation Relocation: More Complex and Controversial".
*Radiology*, 1994, Charles P. Semba, MD, et al, "Iliofemoral Deep Venous Thrombosis: Aggressive Therapy with Catheter-directed Thrombolysis".
*Journal of Vascular Surgery*, Sep. 1999, Thomas S. Huber, MD, PhD, et al, "Impact of race on the treatment for peripheral arterial occlusive disease".
*Abstract, The Annals of Thoracic Surgery*, 1985, J. M. Revuelta, M.D., Ph.D., et al, "Implantation of Pericardial Substitutes".
*Eur J Vasc Endovasc Surg*, 1998, J. May, et al, "Importance of Graft Configuration in Outcome of Endoluminal Aortic Aneurysm Repair: a 5-Year Analysis by the Life Table Method".
*Cardiovascular Surgery*, Apr. 1996, D. Goosens, et al, "'In Vivo' size of knitted Dacron prostheses (Gelseal®) used in the thoracic aorta: a computed tomography study".
*Thrombosis Research*, 1994, Christian Beythien, et al, "In Vitro Model to Test the Thrombogenicity of Coronary Stents".
*Journal of Vascular Surgery*, Jun. 2000, Stavros Kalliafas, MD, et al, "Incidence and treatment of intraoperative technical problems during endovascular repair of complex abdominal aortic aneurysms".
*Transluminal Angioplasty*, Jul. 1990, H. G. Beebe, MD et al, "Indications for Transluminal Angioplasty: A Surgical View".
*Clinical Science*, 1980, R. J. Hawker, et al, "Indium ($^{111}$In)-labelled human platelets: optimal method".
*Abstract, 44th Annual Meeting of the Scnadinavian Association for Thoracic Surgery*, 1995, E. Fosse, et al, "Heparin Coating of Cardiopulmonary Bypass Circuit Reduces Complement Activation, but Does Not Affect the Release of Granulocyte Enzymes in Fully Heparinized Patients—An European MultiCenter Study".
*Circulation*, Jul. 25, 2000, Hideo Tarnai, MD, et al, "Initial and 6-Month Results of Biodegradable Poly-*l*-Lactic Acid Coronary Stents in Humans".
*JACC*, Dec. 1997, Kevin F. Browne, MD, FACC, et al, "Initial Experience With Reuse of Coronary Angioplasty Catheters in the United States".
*Stent Forum, International Edition*, Apr. 1993.
*The American Journal of Surgery*, Jul. 1987, John E. Connolly, MD, "In-Situ Saphenous Vein Bypass: 1962-1987".
*British Journal of Anaesthesia*, Apr. 1997, A. B. Baker, et al, "Intentional asystole during endoluminal thoracic aortic surgery without cardiopulmonary bypass".
*International Congress VII Endovascular Interventions*, Feb. 13-17, 1994, Preliminary Program.
*International Congress. Endovascular Interventions*, 1998, Program and Compilation of abstracts.
*International Congress. Endovascular Interventions*, 2001, Program and Compilation of abstracts.
*International Congress. Endovascular Interventions*, 2002, Program and Compilation of abstracts.
*IES '94 International Endovascular Symposium '94*, Program and Compilation of abstracts.

*International Endovascular Symposium*, Dec. 14-16, 1997, Program and Compilation of abstracts.
*International Society for Endovascular Surgery European Summer Meeting*, Jun. 29-30, 1996, Program and Compilation of abstracts.
*Intervention*, Jul. 1998, C G Sreenivas et al, "Intervention: Carotid Stenting Using a Wallstent".
*Radiology*, 1992, Jean Claude Laborde, MD, et al, "Intraluminal Bypass of Abdominal Aortic Aneurysm: Feasibility Study".
*Radiology*, 1988, Julio C. Palmaz, MD, et al, "Intraluminal Stents in Atherosclerotic Iliac Artery Stenosis: Preliminary Report of a Multicenter Study".
*Circulation*, Oct. 1995, Alvaro Moura, MD, et al, "Intramural Delivery of Agent via a Novel Drug-Delivery Sleeve Histological and Functional Evaluation".
*J Cardiovasc Surg.*, 1987, John D. Corson, et al, "Intra-operative and post-operative flow in the in-situ saphenous vein bypass".
*Angiology*, 1990, Geoffrey H. White, M.D., et al, "Intraoperative Coronary Angioscopy: Development of Practical Techniques".
*Aust. N.Z. J. Surg*, 1993, Peter J. Stewart, et al, "Intra-Operative Ultrasound for the Detection of Hepatic Metastases from Colorectal Cancer".
*Journal of Vascular Surgery*, 1987, Geoffrey H. White, M.D., et al, "Intraoperative video angioscopy compared with arteriography during peripheral vascular operations".
*Cardio*, Dec. 1987, Richard A. Schatz, M.D., et al, "Intravascular Stents for Angioplasty".
*The New England Journal of Medicine*, Mar. 19, 1987, Ulrich Sigwart, M.D., et al, "Intravascular Stents to Prevent Occlusion and Restenosis After Transluminal Angioplasty".
*Cardiovascular Surgery*, Jun. 1997, D. B. Nunn, et al, "Intrinsic Dacron graft failure 19 years post-implantation".
*Cardiology Clinics of North America*, Aug. 1988, Richard A. Schatz, MD, "Introduction to Intravascular Stents".
*Acad Radiol*, 1996, Phillip Harnish, PhD et al, "Iodixanol and the Heart".
*The American Journal of Surgery*, Aug. 1999, Hasan H. Dosluoglu, MD, et al, "Isolated Iliac Artery Aneurysms in Patients with or without Previous Abdominal Aortic Aneurysm Repair".
*Journal of Vascular Surgery*, Feb. 1993, James May, MS, FRACS, FACS, et al, "Isolated limb perfusion with urolinase for acute ischemia".
*Journal of Endovascular Surgery*, 1997, Editorial Board Meeting minutes, and attached articles.
*Journal of Endovascular Therapy*, Oct. 2001, Geoffrey H. White, MD, "What Are the Causes of Endotension?"
*Journal of Vascular and Interventional Radiology*, Sep.-Oct. 1997, Miscellaneous author's abstracts.
*Journal of Vascular Surgery*, Jan. 1994, Information for Authors.
*Journal of Vascular Surgery*, Mar. 2000, G. W. H. Schurink, MD, et al, "Thrombus within an aortic aneurysm does not reduce pressure on the aneurysmal wall".
*Journal of Vascular Surgery*, Mar. 2000, John K. Politz, MD, et al, "Late abdominal aortic aneurysm rupture after AneuRx repair: A report of three cases".
*Journal of Vascular Surgery*, May 2000, Christopyher K. Zarins, MD, et al, "Aneurysm rupture after endovascular repair using the AneuRx stent graft".
*Laser and Stent Therapy in Vascular Disease International Congress II*, Feb. 10-15, 1989, Nurses' Training Course Curriculum.
*Lasers in Cardiovascular Disease*, © 1987, Rodney A. White, et al; Chapter 8, "Laser Vascular Anastomotic Welding".
*Lasers in Cardiovascular Disease*, © 1987, Rodney A. White, et al; Chapter 11—"Laser-Assisted Vascular Anastomoses"; Chapter 13—"Angiscopy"; and Chapter 15—"Perspectives for Development of Angioplasty Guidance Systems".
*Journal of Vascular Surgery*, Mar. 2000, John K.Politz, MD, et al, "Late abdominal aortic aneurysm rupture after AneuRx repair: A report of three cases".
*Arch Surg*, 1984, Magruder C. Donaldson, MD, "Lessons From Initial Experience With the In-Situ Saphenous Vein Graft".
*Surgical Rounds*, May 1987, Letters to the Editor.
*Stroke*, 1996, Jay S. Yadav, MD, et al, "Angioplasty and Stenting for Restenosis After Cartoid Endarterectomy Initial Experience".
*Br. J. Surg.*, 1984, K. K. Sethia et al, "Long saphenous incompetence as a cause of venous ulceration".
*J Thorac Cardiovasc Surg*, 1988, Yorikazu Harada, MD, et al, "Long-term results of the clinical use of an expanded polytetrafluoroethylene surgical membrane as a pericardial substitute".
*Radiology*, 1989, Christian Vallbracht, MD, et al, "Low-Speed Rotational Angioplasty in Chronic Peripheral Artery Occlusions: Experience in 83 Patients".
*E.A.G. Endovascular Aortic Grafting*, Sep. 13, 1996, Program and selected abstracts.
*Malmö International Symposium*, Jan. 29-30, 1999, Program and selection of abstracts.
*Aust. N.Z. J. Surg*, 1997, Michael Wilson, et al, "Management of Acute Vascular Graft Thrombus Associated With Hit Syndrome: A Case Report".
*The New England Journal of Medicine*, Oct. 1989, Thomas E. Starzl, MD, et al, "Medical Progress—Liver Transplantation".
*Proceedings of the Second International Conference on Shape Memory and Superelastic Technologies*, 1997, Stephen J. Kleshinski et al, "Medical Stenting: A Synthesis of Design Principles".
*Medtronic 1998 Annual Report Company Overview*.
*Annals of Surgery*, Sep. 1997, Rodney A. White, M.D., et al, "Modular Bifurcation Endoprothesis for Treatment of Abdominal Aortic Aneurysms".
*Journal of Vascular Surgery*, Aug. 1998, Geert Maleux, MD, et al, "Modular component separation and reperfusion of abdominal aortic aneurysm sac after endovascular repair of the abdominal aortic aneurysm: A case report".
*The Lancet*, Nov. 1998, "Mortality results for randomised controlled trial of early elective surgery or ultrasonographic surveillance for small abdominal aortic aneurysms".
*J Endovasc Surg*, 1995, Timothy A. M. Chuter, MD, "Moving Beyond Conventional".
*Arch Surg*, 1984, Syde A. Taheri, MD, et al, "Muscle Changes in Venous Insufficiency".
*Journal of Vascular Surgery*, 1988, James W. Richardson, MD, et al, "Natural history and management of iliac aneurysms".
*Journal of Vascular Surgery*, 1991, David F. J. Tollefson, MD, et al, "Natural history of atherosclerotic renal artery stenosis associated with aortic disease".
*Int Surg*, 1988, Robert Guidoin, Ph.D., et al, "New Frontiers of Vascular Grafting".
*The Journal of Care Management*, 1995, Warren E. Todd, "New Mindsets in Asthma: Interventions and Disease Management".
*Eur J Vasc Endovasc Surg*, 1996, Charles M. Fisher, et al, "No Additional Benefit from Laser in Balloon Angioplasty of the Superficial Femoral Artery".
*The New England Journal of Medicine*, 1999, Christoph A. Nienaber, M.D., et al, "Nonsurgical Reconstruction of Thoracic Aortic Dissection by Stent-Graft Placement".
*Radiology*, 1987, Julio C. Palmaz, MD, et al, "Normal and Stenotic Renal Arteries: Experimental Balloon-expandable Intraluminal Stenting".
*North American Chapter, International Society for Cardiovascular Surgery 44th Annual Meeting*, Jun. 9-12, 1996, Society for Vascular Surgery, 50th annual Meeting, Poster Outline and Abstracts.
*Current Interventional Cardiology Reports*, 1999, Paul F. Petrasek, MD, FRCSC, et al, "Novel Aortic Reconstruction Strategies: Endovascular Aneurysm Repair".
Official Journal of the European Communities, Dec. 7, 1993, "Council Directive 93/42/EEC of Jun. 14, 1993 concerning medical devices".
*Official Journal of the European Communities*, Jun. 1975, Index.
*JCOM*, May/Jun. 1996, Michael R. Toscani, PharmD, et al, "Onychomycosis: A Disease Management Perspective".
*J Endovasc Surg*, 1997, Christopher K. Zarins, MD, et al, "Operative Repair for Aortic Aneurysms: The Gold Standard".
*To be presented at the 8th Symposium on Echocardiography*, Jun. 21-24, 1989, R.J. Crowley, et al, "Optimized Ultrasound Imaging Catheters for Use in the Vascular System".
*Radiology*, 1993, Andrew H. Cragg, MD, et al, "Percutaneous Femoropopliteal Graft Placement".

*Journal of Vascular and Interventional Radiology*, 1991, Gary J. Becker, MD, et al, "Percutaneous Placement of a Balloon-expandable Intraluminal Graft for Life-Threatening Subclavian Arterial Hemorrhage".

*Journal of Vascular and Interventional Radiology*, Jul.-Aug. 1993, Edward L. Siegel, MD,et al, "Percutaneous Transfemoral Retrieval of a Free-Floating Titanium Greenfield Filter with an Amplatz Goose Neck Snare".

*Journal of Vascular and Interventional Radiology*, Sep.-Oct. 1993, Veronica J. Harris, MD, et al, "Percutaneous Transhepatic Drainage of the Nondilated Biliary System".

*Arch Surg*, Jun. 1981, Thomas D. Brandt, MD, et al, "Percutaneous Transluminal Angioplasty".

*The American Surgeon*, Aug. 1977, Amos D. Tackett, M.D., et al, "Vascular Injuries to the Extremities".

*Coronary Stenting*, 1996, S. S. Yadav, et al, "Percutaneous Treatment of Extracranial Carotid Disease With Angioplasty and Stenting".

*Radiology*, 1989, "Percutaneously Placed Endovascular Grafts for Aortic Aneurysms: Feasibility Study".

*Ann Thorac Surg*, Nov. 1988, William H. Heydorn, M.D., COL, MC, et al, "Pericardial Substitutes: A Survey".

*International Society for Endovascular Surgery European Summer Symposium*, Jun. 27 [*year not noted*] "Session III Perioperative Management of Abdominal Aortic Aneurysm Endoluminal Repair"; "Session IV Aortoiliac Disease"; Session V Aortoiliac Disease; "Session VI Iliofemoropopliteal Disease".

*Hartline* (*A service of the Arizona Heart Institute & Foundation*), 1991, "Peripheral Vascular Disease".

*79th Annual Clinical Congress*, San Francisco, Oct. 10-15, 1993, "Peripheral Vascular Surgery Postgraduate Course" [Index; program; abstracts].

*Journal of Vascular Surgery*, Aug. 1998, Timothy Resch, MD, et al, Persistent collateral perfusion of abdominal aortic aneurysm after endovascular repair does not lead to progressive change in aneurysm diameter.

*Radiology*, 1991, Karim Valji, MD, et al, "Pharmacomechanical Thrombolysis and Angioplasty in the Management of Clotted Hemodialysis Grafts: Early and Late Clinical Results".

*Journal of Vascular and Interventional Radiology*, May-Jun. 1993, Haraldur Bjarnason, MD, et al, "Placement of the Palmaz Stent with Use of an 8-F Introducer Sheath and Olbert Balloons".

*Radiology*, Apr. 1998, Book Review of "Textbook of Metallic Stents" by Robert F. Dondelinger, MD, et al.

*Radiology*, 1998, David F. Kallmes, MD, et al, "Platinum Coil-mediated Implantation of Growth Factor-secreting Endovascular Tissue Grafts: An in Vivo Study".

*Arch Surg*, Nov. 1980, Leonardo T. Lim, MD, et al, "Popliteal Artery Trauma".

*European Journal of Vascular Endovascular Surgery*, 1991, K. J. Dawson, et al, "Popliteal Vein Aneurysm".

*Journal of vascular and Interventional Radiology*, Jan.-Feb. 1993, K. Nakamura, MD, et al, "Portal Decompression After Transjugular Intrahepatic Portosystemic Shunt Creation with Use of a Spiral Z Stent".

*Journal of Vascular Surgery*, Sep. 1990, Daniel B. Nunn, MD, et al, "Postoperative dilation of knitted Dacron aortic bifurcation graft".

*Br J Surg*, 1982, T. Christensen, et al, "Fatigue and cardiorespiratory function following abdominal surgery".

*Br J Surg*, 1985, T. Christensen, et al, "Influence of pre- and intra-operative factors on the occurrence of postoperative fatigue".

*World J Surg*, 1993, Tom Christensen, M.D., et al, "Postoperative Fatigue".

*Eur J Vasc Endovasc Surg*, May 1998, I. Syk, et al, "Postoperative Fever, Bowel Ischaemia and Cytokine Response to Abdominal Aortic Aneurysm Repair—a Comparison Between Endovascular and Open Surgery".

*Journal of Vascular Surgery*, Jun. 1988, Samuel S. Ahn, M.D., et al, "Postoperative thrombotic complications in patients with the lupus anticoagulant: Increased risk after vascular procedures".

*Surgery, Gynecology \* Obstetrics*, Feb. 1991, Robert L. Heyd, M.D., et al, "Preventing Kinking of the Peel-Away Sheath During Insertion of a Long Term Central Venous Catheter Using Percutaneous Subclavicular Venipuncture".

*The New England Journal of Medicine*, Oct. 12, 1989, Martin P. Nevitt, M.P.H., et al, "Prognosis of Abdominal Aortic Aneurysms a Population-Based Study".

*ISES—European Summer Symposium Global Endovascular Approach in the Treatment of Vascular Disease*, Jun. 20-23, 2000, Program.

*European Heart Journal*, 1995, H. Hanke, et al, "Prolonged proliferative response of smooth muscle cells after experimental intravascular stenting".

*Eur J Vasc Endovasc Surg*, 1995, I. M. Williams, et al, "Pseudoaneurysm of the Thoracic Aorta: Missed Traumatic Rupture".

*J Cardiovasc Surg.*, 1989, V .S. Sottiurai, M.D., Ph.D., et al, "Pseudointima formation in woven and knitted dacron grafts A comparative ultrastructural analysis".

*Journal of Endovascular Surgery*, 1999, Gareth D. Treharne, FRCS, et al, "Quality Control During Endovascular Aneurysm Repair: Monitoring Aneurysmal Sac Pressure and Superficial Femoral Artery Flow Velocity".

*Journal of Vascular Surgery*, Dec. 1989, Spiros N. Vasdekis, MD, et al, "Quantification of venous reflux by means of duplex scanning".

*Surgery*, Dec. 1982, John J. Bergan, M.D., et al, "Randomization of autogenous vein and polytetrafloroethylene grafts in femoral-distal reconstruction".

*Journal of Vascular Surgery Online*, Jul. 2000, Yehuda G. Wolf, MD, et al, "Rate of change in abdominal aortic aneurysm diameter after endovascular repair".

*Journal of Vascular Surgery*, Sep. 1997, Robert F. Rutherford, MD, et al, "Recommended standards for reports dealing with lower extremity ischemia: Revised version".

*Journal of Endovascular Surgery*, 1999, Juan C. Parodi, MD, et al, "Relocation of the Iliac Artery Bifrucation to Facilitate Endoluminal Treatment of Abdominal Aortic Aneurysms".

*Euro J Vasc Endovasc Surg*, Aug. 1997, M. Malina, et al, "Renal Arteries Covered by Aortic Stents: Clinical Experience From Endovascular Grafting of Aortic Aneurysms".

*British Journal of Surgery*, Nov. 1996, James May, et al, "Repair of abdominal aortic aneurysms by the endoluminal method: outcome in the first 100 patients".

*Journal of Endovascular Therapy*, 2000, Edward V. Kinney, MD, et al, "Repair of Mycotic Paravisceral Aneurysm With a Fenestrated Stent-Graft".

*Seminars in Vascular Surgery*, Dec. 1997, Robert B. Rutherford, "Reporting Standards for Endovascular Surgery: Should Existing Standards Be Modified for Newer Procedures?"

*Journal of Vascular Surgery*, Feb. 1997, Samuel S. Ahn, MD, et al, "Reporting standards for infrarenal endovascular abdominal aortic aneurysm repair".

*Journal of Vascular Surgery*, Jun. 1993, Samuel S. Ahn, MD, "Reporting standards for lower extremity arterial endovascular procedures".

*Research Digest on Vascular Disease*, Aug. 1988, A compendium of abstracts from the recent medical literature.

*Abstract*, Feb. 1997, Kenneth Rosenfield, MD, FACC., et al, "Restenosis of Endovacular Stents From Stent Compression".

*Journal of Vascular Surgery*, Sep. 1991, Lazar J. Greenfield, MD, et al, "Results of a multicenter study of the modified hook-titanium Greenfield filter".

*Journal of Vascular Surgery*, Jun. 2000, Willem Wisselink, MD, PhD., et al, Retroperitoneal endoscopic litigation of lumbar and inferior mesenteric arteries as a treatment of persistent endoleak after endoluminal aortic aneurysm repair.

*Journal of Vascular Surgery*, Jan. 1984, Gerald M. Lemole, M.D., et al, "Rigid intraluminal prosthesis for replacement of thoracic and abdominal aorta".

*Journal of Vascular Surgery*, Mar. 2001, Takuya Hatakeyama, MD, et al, "Risk factors for rupture of abdominal aortic aneurysm based on three-dimensional study".

*Eur J Vasc Endovasc Surg*, 1999, J. May, et al, "Rupture of Abdominal Aortic Aneurysms: A Concurrent Comparison of Outcome of Those Occurring After Endoluminal Repair Versus Those Occuring De Novo".

*Cancer Treatment Reports*, Jul. 1978, Robert Makuch et al, "Sample Size Requirements for Evaluating a Conservative Therapy".
*Drug Information Journal*, 1995, Stan C. Lin, PhD. "Sample Size for Therapeutic Equivalence Based on Confidence Interval".
*Seminars and Vascular Surgery*, Dec. 1999, H. G. Beebe et al, "Screening and Preoperative Imaging of Candidates for Conventional Repair of Abdo minal Aortic Aneurysm".
*Surgical Clinics of North America*, Aug. 1989, Joseph J. Piotrowski, M.D., et al, "Selection of Grafts Currently Available for Repair of Abdominal Aortic Aneurysms".
*Radiology*, Jan. 1990, Alison Gillams, MB, ChB, MRCP, FRCR, et al, "Self-expandable Stainless Steel Braided Endoprosthesis for Biliary Strictures".
*Endoscopy*, Sep. 1989, H. Neuhaus, et al, "Self-expanding Biliary Stents: Preliminary Clinical Experience".
*Surgery, Gynecology & Obstetrics*, Feb. 1991, John L. Ricci, M.D., F.A.C.S., et al, "The Surgeon at Work Simple Technique for Long Term Central Venous Access in the Patient With Thrombocytopenic Carcinoma".
*Department of Surgery, University of Sydney and Department of Vascular Surgery, Royal Prince Alfred Hospital*, 2000, Geoffrey H. White, et al, "Specific complications of endovascular aortic repair".
*Journal of Interventional Radiology*, 1989, R. Dick, et al, "Stainless Steel Mesh Stents for Biliary Strictures".
*The Journal of Vascular Technology*, 1991, Marcia S. Foldes, B.S.N., R.V.T., et al, "Standing Versus Supine Positioning in Venous Reflux Evaluation".
*J Endovasc Ther*, 2000, Scheinert, MD, et al, "Statement of Catheter-Induced Iliac Artery Injuries With Self-Expanding Endografts".
*BT Alex. Brown Research*, 1998, Jonathan W. Osgood, CFA, et al, "Abdominal Aortic Aneurysms".
*Indian PTCA Registry Meeting*, Apr. 1996, Dr. J. Venkateswarlu, "Stenting of Abdominal Aorta and Coil Embolization of Aneurysm".
*CardioVascular and Interventional Radiology*, 1992, Julio C. Palmaz, et al, "Stenting of the iliac Arteries with the Palmaz Stent: Experience from a Multicenter Trial".
*Endovascular Update*, 1998, Jan Bart Hak, et al, "Study update—The PRECISE and CRISP studies of PERFLEX™ and SMART™ endovascular stents".
*Circulation*, 1996, Sushil Sheth, MD, et al, "Subacute Thrombosis and Vascular Injury Resulting From Slotted-Tube Nitinol and Stainless Steel Stents in a Rabbit Carotid Artery Model".
*Journal of Endovascular Surgery*, 1999, Laura H. Phipp, FRCS, et al, "Subclavian Stents and Stent-Grafts: Cause for Concern?"
*Surgery*, Dec., 1977, Ronald J. Baird, MD, et al, "Subsequent downstream repair after aorta-iliac and aorta-femoral bypass operation".
*Journal of Vascular Surgery*, Jul. 1995, Joseph S. Coselli, MD, et al, "Subsequent proximal aortic operations in 123 patients with previous infrarenal abdominal aortic aneurysm surgery".
*Journal of Endovascular Surgery*, 1997, Zvonimir Krajcer, MD, et al, "Successful Endoluminal Repair of Arterial Aneurysms by Wallstent Prosthesis and Ptfe Graft: Preliminary Results With a New Technique".
*Surgery*, Jul. 1955, Jack A. Cannon, M.D., et al, "Successful Management of Obstructive Femoral Artericosclerosis by Endarterectomy".
*Journal of Endovascular Surgery*, Mar. 1991, K. Wayne Johnston, MD, et al, "Suggested standards for reporting on arterial aneurysms".
*Journal of Endovascular Surgery*, Jul. 1986, Robert B. Rutherford, MD, et al, "Suggested standards for reports dealing with lower extremity ischemia".
*Annals of Vascular Surgery*, 2005, Mark Robbins, MD, et al, "Suprarenal Endograft Fixation Avoids Adverse Outcomes Associated with Aortic Neck Angulation".
*International Society for Endovascular Surgery, European Summer Symposium*, 1996, EB Diethrich, "Carotid Angioplasty: an Endovascular Surgeon's Point of View".
*International Society for Endovascular Surgery, European Summer Symposium*, 1996, GM Biasi, "Carotid Angioplasty: A Surgeon's Point of View".
*International Society for Endovascular Surgery, European Summer Symposium*, 1996, H Spoelstra, et al, "Double-Stented Balloon-Expandable Endobypass Technique for Popliteal Aneurysmal Disease".
*International Society for Endovascular Surgery, European Summer Symposium*, 1996, F. Citterio, et al, "Endovascular Treatment of Limb Threatening Ischemia".
*International Society for Endovascular Surgery, European Summer Symposium*, 1996, JP Becquemin, et al, "Update on the STAF Study".
*International Society for Endovascular Surgery, European Summer Symposium*, 1996, A Bray, "Duplex Ultrasound Assessment Following Angioplasty for Occlusive Arterial Disease".
*International Society for Endovascular Surgery, European Summer Symposium*, 1996, JP Becquemin, MD, et al, "Surgical Transluminal Iliac Angioplasty with Selective Comparison with Surgery".
*International Society for Endovascular Surgery, European Summer Symposium*, 1996, M Enzler, et al, "Computer Registry for the European Study on Stent-Graft Techniques for Abdominal Aortic Aneurysm Repair (EUROSTAR)".
*International Society for Endovascular Surgery, European Summer Symposium*, 1996, P. Harris, et al, "Methodology for Abdominal Aortic Aneurysm Endovascualr Repair Studies".
*International Society for Endovascular Surgery, European Summer Symposium*, 1996, JC Parodi, et al, "Long-term Follow-up of Abdominal Aortic Aneurysm Endoluminal Repair".
*International Society for Endovascular Surgery, European Summer Symposium*, 1996, DB Reid, et al, "Carotid Morphological Selection for Endoluminal Repair".
*International Society for Endovascular Surgery, European Summer Symposium*, 1996, H van Urk, "Methodologies of Carotid Endoluminal Repair Studies".
*International Society for Endovascular Surgery, European Summer Symposium*, 1996, Chantal Levasseur, "Highly performing technicians in the operating theatre, but also . . . what type of training and what is at stake?"
*International Society for Endovascular Surgery, European Summer Symposium*, 1996, Chantal Levasseur, "En bloc opératoire des technicians performants, mais aussi . . . quelle formation pour quells enjeux?"
*International Society for Endovascular Surgery, European Summer Symposium*, 1996, Chantal Peyrouzet, "Nurse Management for Endovascular Treatment of AAA Using a Bifurcated Covered Stent."
*Journal of Vascular Surgery*, 1994, Philippe Piquet, MD, et al, "Tantalum-Dacron coknit stent for endovascular treatment of aortic aneurysms: a preliminary experimental study".
*Radiology*, 1983, Charles T. Dotter, M.D., et al, "Transluminal Expandable Nitinol Coil Stent Grafting: Preliminary Report".
*Journal of Vascular Surgery*, 1987, Rodney A. White, M.D., "Technical frontiers for the vascular surgeon: Laser anastomotic welding and angioscopy-assisted intraluminal instrumentation".
*Department of Radiology, University of Minnesota Hospitals*, 1982, Andrew Cragg, M.D., "Nonsurgical Placement of Arterial Endoprostheses: A New Technique Using Nitinol Wire".
Artif Organs, 1997, page of abstracts.
*Eur J Vasc Endovasc Surg*, 1999, J. May, et al, "Techniques for Surgical Conversion of Aortic Endoprosthesis".
*Journal of Vascular Surgery*, Feb. 2001, Christopher K. Zarins, MD, et al, "The AneuRx stent graft: Four-year results and worldwide experience 2000".
*Sulzer Medica Journal*, Feb. 1998, Stuart Rodger et al, "The Changing Face of Aneurysm Surgery".
*Surgery*, Jan. 1986, William C. Mackey, M.D., et al, "The costs of surgery for limb-threatening ischemia".
*Journal of Vascular Surgery*, Jun. 2000, Richard J. Powell, MD, et al, "The durability of endovascular treatment of multisegment iliac occlusive disease".
*Journal of Vascular Surgery*, Jun. 1991, William L. Breckwoldt, MD, et al, "The economic implications of high-risk abdominal aortic aneurysms".
*Eur J Vasc Endovasc Surg*, Feb. 1997, T. Whitbread, et al, "The Effect of Placing and Aortic Wallstent Across the Renal Artery Origins in an Animal Model".
*New Medicine*, 1997, Kent W. Peterson, MD, et al, "The Evolution of Disease Management Into Population-Based Health Management".
*Barcelona ESVS Meeting*, Sep. 1993, J. Mayu's notes from Dr. parodi's presentation.

*Buenos Aires*, Sep. 1992, Dr. Parodi's own drawings from discussion with J. May.
*Buenos Aires*, Sep. 1992, J. May's notes from discussion with Dr. Parodi.
*Journal of Endovascular Surgery*, 1997, Wesley S. Moore, MD, "The EVT Tube and Bifurcated Endograft Systems: Technical Considerations and Clinical Summary".
*Journal of Vascular Surgery*, Oct. 1990, Joseph L. Mills, MD, et al, "The importance of routine surveillance of distal bypass grafts with duplex scanning: A study of 379 reversed vein grafts".
*The International Society of Cardiovascular Surgery. 42nd Scientific Meeting*, Jun. 1994, Program.
*Journal of Vascular Surgery*, Jun. 1999, Christopher K. Zarins, MD, "The limits of endovascular aortic aneurysm repair".
*Journal of Vascular Surgery*, Feb. 1999, Zarins et al, "AneuRx stent graft versus open surgical repair of abdominal aortic aneurysms: Multicenter prospective clinical trial".
*Journal of Vascular Surgery*, Nov. 1988, Debra Graham, MD, et al, "The management of localized abdominal aortic dissections".
*Journal of Endovascular Surgery*, 1995, Gwan H. Ho, MD, et al, "The Mollring Cutter™ Remote Endarterectomy: Preliminary Experience With a New Endovascular Technique for Treatment of Occlusive Superficial Femoral Artery Disease".
*The New England Journal of Medicine*, Feb. 1998, Hervé Decousus, MD, et al, "A Clinical Trial of Vena Caval Filters in the Prevention of Pulmonary Embolism in Patients With Proximal Deep-Vein Thrombosis".
*The New England Journal of Medicine*, 1958, William P. Longmire, Jr., M.D., et al, "Direct-Vision Coronary Endarterectomy for Angina Pectoris".
© *1990 Olympus Corporation*, "The Olympus Valvulotomes for Angioscopically Assisted in Situ Bypass. A Cut Above in Precision Valvulotomy".
*Cardiovascular Surgery*, 1998, M. Lawrence-Brown, et al, "The Perth HLB bifurcated endoluminal graft: A review of the experience and intermediate results".
*The American Journal of Surgery*, 1999, Richard M. Young, MD, et al, "The Results of In Situ Prosthetic Replacement for Infected Aortic Grafts".
*Cardiovascular Surgery*, 1995, W. S. Moore, "The role of endovascular grafting technique in the treatment of infrarenal abdominal aortic aneurysm".
*World Journal of Surgery*, 1986, James S. T. Yao, M.D., Ph.D., et al, "The Role of Noninvasive Testing in the Evaluation of Chronic Venous Problems".
*Surgery*, 1982, M. C. Hoare, F.R.A.C.S., et al, "The role of primary varicose veins in venous ulceration".
*The Society for Vascular Surgery, 52nd Annual Meeting, The San Diego Convention Center*, 1998, Program.
*The American Journal of Surgery*, 1999, Eric S. Weinstein, MD, et al, "The 'Stable' Ruptured Abdominal Aortic Aneurysm Gives a False Sense of Security".
*The Journal of Cardiovascular Surgery*, 1996, F. J. Criado, MD et al, "The surgeon as an endovascular interventionist. Why and how?"
*Journal of Vascular Surgery*, 1999, Jack L. Cronenwett, MD, et al, "The United Kingdom Small Aneurysm Trial: Implications for surgical treatment of abdominal aortic aneurysms".
*Diagnostic & Interventional Radiologym*, 1989, F. Joffre, et al, "The usefulness of an endovascular prosthesis for treatment of renal artery stenosis".
*Journal of Endovascular Surgery*, 1997, Wolf Stelter, MD, PhD, et al, "Three-Year Experience with Modular Stent-Graft Devices for Endovascular AAA Treatment".
*Journal of Vascular Surgery*, 1988, Jack L. Cronenwett, MD, et al, "Tibial artery pseudoaneurysms: Delayed complication of balloon catheter embolectomy".
*Journal of Endovascular Surgery*, 1999, Thomas Umscheid, MD, et al, "Time-Related Alterations in Shape, Position, and Structure of Self-Expanding, Modular Aortic Stent-Grafts: A 4-year Single-Center Follow-Up".
*Journal of Vascular Surgery*, 1993, Timothy A. M. Chuter, BM, BS, "Transfemoral endovascular aortic graft placement".

*Journal of Vascular Surgery*, 1996, Wesley S. Moore, MD, et al, "Transfemoral endovascular repair of abdominal aortic aneurysm: Results of the North American EVT phase 1 trial".
*The American Journal of Surgery*, 1995, Michael L. Marin, MD, et al, "Transfemoral Endovascular Repair of Iliac Artery Aneurysms".
*Annals of Vascular Surgery*, 1991, J. C. Parodi, MD, et al, "Transformal Intraluminal Graft Implantation for Abdominal Aortic Aneurysms".
*Journal of Surgical Research*, 1986, Alexander Balko, M.D., et al, "Transfemoral Placement of Intraluminal Polyurethane Prosthesis for Abdominal Aortic Aneurysm".
*J Thorac Cardiovasc Surg*, 1990, William Evans Neville, MD, et al, "Clinical experience with the silicone tracheal prosthesis".
*The American Journal of Surgery*, Aug. 1989, Mehmet C. Oz, MD., et al, "Replacement of the Abdominal Aorta With a Sutureless Intraluminal Ringed Prosthesis".
*Monthly Scientific and Practical Journal*, vol. 137, 1986, I.I. Grekov Surgery Bulletin.
*International Congress on Thoracic and Thoracoabdominal Aortic Aneursym*, Jun. 1994, J. May, et al, "Transluminal placement of aortoiliac grafts for treatment of large abdominal aortic aneurysms".
*Radiology*, 1989, Hervé P. Rousseau, MD, et al, "Treatment of Femoropopliteal Stenoses by Means of Self-expandable Endoprostheses: Midterm Results".
*Gastrointestinal Endoscopy*, 1992, John Schaer, MD, et al, "Treatment of malignant esophageal obstruction with silicone-coated metallic self expanding stents".
*Abdominal Aortic Aneurysms, Surgical Clinics of North America*, 1989, Kaj Johansen, M.D., Ph.D., "Treatment Options for Aneurysms in High-Risk Patients".
*International Workshop on Endovascular Surgery*, 1997, G. Coppi, et al, "Treatment, Using Endograft, of 6 Cases of Aneurysms of the Descending Thoracic Aorta."
*Journal of Endovascular Surgeryery*, 1997, Ulrich Blum, MD, et al, "Two-Center German Experience With Aortic Endografting".
*CardioVascular and Interventional Radiology*, 1987, David R. Hassell, et al, "Unilateral Left Leg Edema: A Variation of the May-Thurner Syndrome".
*JVIR*, Sep. 1999, Richard G. McWilliams, FRCS, FRCR, "Use of Contrast-enhanced Ultrasound in Follow-Up after Endovascular Aortic Aneurysm Repair".
*The American Journal of Surgery*, 1999, Christopher G. Carsten III, MD, et al, "Use of Limited Color-Flow Duplex for a Cartoid Screening Project".
*Journal of Vascular and Interventional Radiology*, 1997, Noriyuki. Kato, MD, et al, "Use of a Self-Expanding Vascular Occluder for Embolization During Endovascular Aortic Aneurysm Repair".
*Anaesthesia and Intensive Care*, 1991, G. Brown, et al, "Use of the Cell Saver During Elective Abdominal Aortic Aneurysm Surgery—Influence on Transfusion with Bank Blood. A Retrospective Survey".
*Reoperative Arterial Surgery*, 1986, James May et al, "Use of the Supraceliac Abdominal Aorta for Repeat Aortic Surgery".
*Journal of Validation Technology*,1997, Dennis Christensen et al., "Validation of Emerging Technology Sterilizers".
© 1994 *IMPRA*, E. D. Schwilden, "Vascular Anastomotic Techniques".
*Radiology*, May 1994, Jon G. Moss, FRCR, et al, "Vascular Occlusion with a Balloon-Expandable Stent Occluder".
*Journal of Endovascular Therapy*, 2000, Marc R.H.M. van Sambeek, MD, et al, "Vascular Response in the Femoropopliteal Segment After Impantation of an ePTFE Balloon-Expandable Endovascular Graft: An Intravascular Ultrasound Study".
*Circulation*, 1989, Spencer B. King III, MD, "Vascular Stents and Atherosclerosis".
*Vascular Surgery*, Sep. 1994, Martin R. Back, M.D., et al, "Endoluminal Placement of PTFE Graft-Stent Devices in a Canine Model".
*Vector Securities International*, May 1998, David A. Gruber, M.D., et al, "Company Update".
*Venous Disorders*, 1991, "Current Views on the Pathogenesis of Venous Ulceration".
*Radiology*, 1989, Rolf W. Gunther, MD, et al, "Venous Stenoses in Dialysis Shunts: Treatment with Self-expanding Metallic Stents".

Journal of Endovascular Surgery, 1996, Patrick W. Stroman, PhD, et al, "Will it be Feasible to Insert Endoprostheses Under Interventional MRI?"

Workshop on Pre-Clinical Testing for Endovascular Grafts, Jul. 31-Aug. 1, 2001, Agenda.

World Medical: Manufacturing Corporation, May 1998, Newsletter.

Surgical Clinics of North America, Apr. 1986, Mark M. Kartchner, M.D., et al, "Wrapping of Abdominal Aortic Aneurysms: A Viable Alternative".

Journal of Endovascular Therapy, vol. 4, No. 2, pp. 195-202, "What Are the Characteristics of the Ideal Endovascular Graft for Abdominal Aortic Aneurysm Exclusion?"

Transcription and Photographs of video operation submitted to European Patent Office on May 4, 2001 in Opposition of EP 0 686 379 and on May 11, 2001 in Opposition of EP 0 792 627.

Jay Lenker Notebook Pages, Jul. 30, 1993.

Atrium Medical Corp., Changing the Future With Advances in Polymer Chemistry, Plasma TFE™ Sales Development Program and Technical Reference Manual, Jan. 20, 1986.

Atrium Medical Corp., Important Implant Information, Plasma TFE—Straight Synthetic Artery—Directions for Use, May 1, 1986.

Rodney A. White, et al, Peripheral Endovascular Interventions, Chap 26, Combined Surgical and Endovascular Approaches, pp. 433-448, Mosby-Year Book, Inc. (1996).

Rodney A. White, et al, A Color Atlas of Endovascular Surgery, Chap 12, Evolving Technologies, pp. 146-153, Chapman and Hall (1990).

Geoffrey H. White, Complications of Endovascular Repair of AAA, ISCVS 24$^{th}$ World Congress, Melbourne Australia, Sep. 12-16, 1999.

Geoffrey H. White et al, A Comparison of Four Devices for Endoluminal Repair of Abdominal Aortic Aneurysms, Division of Surgery, Royal Prince Alfred Hospital, Sydney, May 1994.

EP Strecker, et al, A Flexible Percutaneously Insertable Vascular Prosthesis, Laser and Stent Therapy in Vascular Disease, International Congress II, 1989.

JB Muhlestein, et al A New Highly Fexible Balloon-Expandable Endovascular Stent: Initial Experimental Results with Follow-up, Laser and Stent Therapy in Vascular Disease, International Congress II, 1989.

Michael R. Jedwab et al, A Study of the Geometrical and Mechanical Properties of a Staff-Expanding Metallic Stent-Theory and Experiment, Journal of Applied Biomaterials, vol. 4, pp. 77-85 (1993).

Renann Uflacker, MD, et al, Abdominal Aortic Aneurysm Treatment: Preliminary Results With the Talent Stent-Graft System, Journal of Vascular and Interventional Radiology, vol. 9, pp. 51-60. Jan.-Feb. 1998.

J. May, et al, Advantages and Limitations of Intraluminal Grafts for Thoracic and Abdominal Aortic Aneurysms, Department of Vascular Surgery, Royal Prince Alfred Hospital and University of Sydney, Fax of abstract Nov. 11, 1992.

JR Crew, et al, Angioscopic Evaluation of Thermal Activated Stents: Experimental and Clinical Results, Laser and Stent Therapy in Vascular Disease, International Congress II, 1989.

Robert C. Shamberger, M.D., et al, Arterial Injuries During Inguinal Herniorrhaphy, Surgical Services, Massachusetts General Hospital, and the Department of Surgery, Harvard Medical School, Nov. 21, 1983.

NJ Lembo, et al, Balloon-Expandable Coil Stent: A Treatment for Acute Closure Post-PTCA, Laser and Stent Therapy in Vascular Disease, International Congress II, 1989.

IM Penn, et al, Balloon-Expandable Intravascular Stents (BEIS) Following Failed Laser Angioplasty of Iliac Arteries, Laser and Stent Therapy in Vascular Disease, International Congress II, 1989.

JC Palmaz, Balloon Expandable Stenting: An Overview of Current Clinical Experience, Laser and Stent Therapy in Vascular Disease, International Congress II, 1989.

RA Schatz, et al, Balloon Expandable Stents in Human Coronary Arteries: Report of Initial Experience, Laser and Stent Therapy in Vascular Disease, International Congress II, 1989.

Georgi Russev Marinov, MD, et al, Can the Infusion of Elastase in the Abdominal Aorta of the Yucatan Miniature Swine Consistently Produce Experimental Aneurysms?, Journal of Investigative Surgery, vol. 10, pp. 129-150, 1997.

Jon S. Matsumura, MD, et al, Clinical consequences of periprosthetic leak after endovascular repair of abdominal aortic aneurysm, Society for Vascular Surgery and International Society for Cardiovascular Surgery, Boston, MA,Jun. 1997.

D. J. Dove-Bigley, et al, Complications associated with in-situ vein grafts for femoropopliteal bypass, Vascular Surgery Unit, Broadgreen Hospital, Liverpool, UK, Buttersworth & Co. Ltd., 1984.

GP Rodgers, et al, Coronary Stent Patency in Swine: Aspirin vs Control, Laser and Stent Therapy in Vascular Disease, International Congress II, 1989.

Selected Abstracts, International Society for Endovascular Surgery, European Summer Symposium, Jun. 1996.

Albert Krause, MD et al, Early Experience With the Intraluminal Graft Prosthesis, The American Journal of Surgery, vol. 145, May 1983.

Selected Abstracts, Journal of Vascular Surgery, vol. 25, No. 1, Jan. 1997.

Rodney A. White, MD, et al, Endovascular surgery credentialing and training for vascular surgeons, Journal of Vascular Surgery vol. 17, p. 1095, 1993.

Geoffrey H. White, M.D., et al, Experimental and Clinical Applications of Angioscopic Guidance for Laser Angioplasty, 41$^{st}$ Annula meeting of he Southwestern Surgical Congress, Monterey, CA Apr. 1989.

J Rösch, et al, Expandable Wire Stents in Treatment of Superior Vena Cava Syndrome, Laser and Stent Therapy in Vascular Disease, International Congress II, 1989.

K. Wayne, Johnston, MD, FRCSC, Femoral and Popliteal Arteries: Reanalysis of Results of Balloon Angioplasty, Radiology, vol. 183, pp. 767-771, 1992.

Dr. Ulrich Blum, et al, Femoral and Popliteal Artery Stenoses and Occlusions: Treatment with Local Thrombolysis, PTA and Intravascular Stents, University Hospital Frieburg, Germany, ED051, 1993.

JE Rabkin, Five-Year Experience in Thermoplastic Nitinol Stent Grafting, Laser and Stent Therapy in Vascular Disease, International Congress II, 1989.

Geoffrey H. White, M.D., et al, In-Situ Saphenous Vein Bypass: Prevention and Management of Early Complications, Department of Surgery, Harbor-UCLA Medical Center, Annual Meeting Southern California Vascular Surgery Society, Sep. 1987.

Rodney A. White, M.D., et al, Laser Vascular Welding—How Does it Work?, Departments of Surgery, Pathology and Medicine, Southern California Vascular Surgical Society Meeting, Sep. 1986.

Rodney A. White, et al, Laser Welding of Large Diameter Arteries and Veins, Department of Surgery and Medicine, Harbor-UCLA Medical Center, Trans Am Soc Artif Intern Organs, 1986.

Alberto Gil-Peralta, MD, et al, Percutaneous Transluminal Angioplasty of the Symptomatic Atherosclerotic Cartoid Arteries Results, Complications and Follow-up, Presented in part at the Fourth European Stroke Conference, Bordeaux, France Jun. 1995.

Kato YP, et al, Preliminary Mechanical Evaluation of a Novel Endoluminal Graft, The 21st Annual Meeting of the Society for Biomaterials, Mar. 1995.

Hugh G. Beebe, M.D, Late Failures of Devices Used for Endovascular Treatment of Abdominal Aortic Aneurysm: What Have We Learned and What is the Task for the Future?, Perspectives in Vascular Surgery and Endovascular Therapy, vol. 14, No. 1, 2001.

Standard Practice for Performance Testing of Shipping Containers and Systems, ASTM Designation: D 4169-06, Aug. 1996.

CS Sutton, et al, Stenting in Normal and Atherosclerotic Rabbits: Studies of the Intravascular Endoprosthesis of Titanium-Nickel Alloy, Laser and Stent Therapy in Vascular Disease, International Congress II, 1989.

Wolf Sapirstein, MD, et al, The Food and Drug Administration approval of endovascular grafts for abdominal aortic aneurysm: An 18-month retrospective, Journal of Vascular Surgery, vol. 34, pp. 180-183, 2001.

G. Szendro, M.D., et al, Duplex scanning in the assessment of deep venous incompetence, Journal of Vascular Surgery, vol. 4, pp. 237-242, 1986.

Randall. K. Wolf, M.D., et al, *Transaxillary intra-aortic balloon tamponade in trauma*, Journal of Vascular Surgery, vol. 4, pp. 95-97, 1986.

*Twenty-Second Annual Symposium on Current Critical Problems, New Horizons and Techniques in Vascular and Endovascular Surgery*, Brochure, Nov. 1995.

A. H. Choudhri, et al, *Unsuspected renal artery stenosis in peripheral vascular disease*, BMJ, vol. 301, pp. 1197-1198, Nov. 1990.

Jack L. Cronenwett, M.D., Arterial Aneurysms, *Vascular Surgery*, $5^{th}$ Edition, Chap. 88, W.B. Saunders Company, 2000.

* cited by examiner

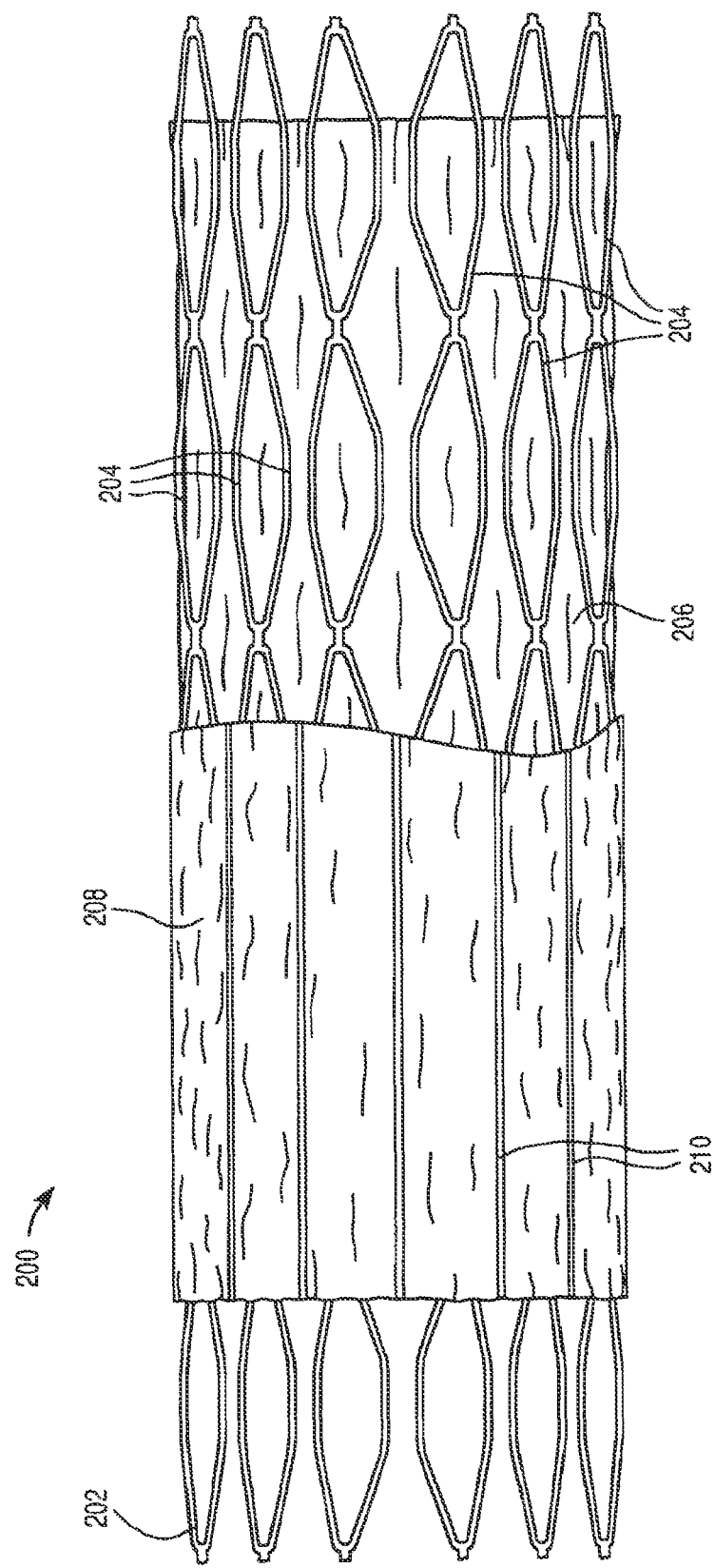

APPARATUS AND METHODS FOR ENDOLUMINAL GRAFT PLACEMENT

This is a Division of application Ser. No. 08/255,681 filed Jun. 8, 1994 now abandoned.

BACKGROUND OF THE INVENTION

1. Field of the Invention

The present invention relates generally to apparatus and methods for endoluminal placement of grafts, stents, and other structures. More particularly, the present invention relates to a low profile, compressible graft structure and apparatus and methods for vascular placement of such structures for the treatment of abdominal and other aneurysms.

Vascular aneurysms are the result of abnormal dilation of a blood vessel, usually resulting from disease and/or genetic predisposition which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and require experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 3% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular graft placement for the treatment of aneurysms has been proposed. Although very promising, many of the proposed methods and apparatus suffer from other problems. Often times the proposed graft structures will have exposed anchors or frame which can be thrombogenic. It is also difficult to provide graft structures which remain sealed to the blood vessel lumen to prevent the leakage or bypass of blood into the weakened aneurysm, especially when subjected to external deforming forces which result from vessel expansion and contraction as the heart beats. Many vascular graft structures have difficulty in conforming to the internal arterial wall, particularly since the wall can have a highly non-uniform surface as a result of atherosclerosis and calcification and is expanding and contracting with the patient's heartbeat and blood flow. Additionally, many previous vascular graft structures are difficult to position and anchor within the target region of the vessel.

For these reasons, it would be desirable to provide improved apparatus and methods for the endovascular placement of intraluminal grafts for treating aneurysms and other conditions. It would be particularly desirable if the graft structures were easy to place in the target region, displayed little or no thrombogenicity, provided a firm seal to the vascular wall to prevent leakage and blood bypass, and were able to conform to uniform and non-uniform blood vessel walls, even while the wall is expanding and contracting with the patient's heartbeat.

2. Description in the Background Art

Vascular grafts and devices for their transluminal placement are described in U.S. Pat. Nos. 5,219,355; 5,211,658, 5,104,399; 5,078,726; 4,820,298; 4,787,899; 4,617,932; 4,562,596; 4,577,631; and 4,140,126; and European Patent Publications 508 473; 466 518; and 461 791.

Expandable and self-expanding vascular stents are described in U.S. Pat. Nos. 5,147,370; 4,994,071; and 4,776,337; European patent Publications 575 719; 556 850; 540 290; 536 610; and 481 365; and German patent Publication DE 42 19 949. A flexible vascular stent structure having counter wound helical elements, some of which are separated at particular locations to enhance flexibility, is commercially available from Angiomed, Karlsruhe, Germany, as described in a brochure entitled Memotherm Iliaca Stents.

Catheters for placing vascular stents are described in U.S. Pat. Nos. 5,192,297; 5,092,877; 5,089,005; 5,037,427; 4,969,890; and 4,886,062.

Vascular grafts intended for open surgical implantation are described in U.S. Pat. Nos. 5,236,447; 5,084,065; 4,842,575; 3,945,052; and 3,657,744; and PCT applications WO 88/00313 and WO 80/02641; and SU 1697787.

Nickel titanium alloys and their use in medical devices are described in U.S. Pat. Nos. 4,665,906 and 4,505,767.

SUMMARY OF THE INVENTION

The present invention comprises apparatus and methods for the endoluminal placement of intraluminal grafts for the treatment of disease conditions, particularly aneurysms. The intraluminal grafts comprise a radially compressible, perforate tubular frame having a proximal end, a distal end, and an axial lumen between said ends. An interior liner, typically a fabric, polymeric sheet, membrane, or the like, covers all or most of the surface of the lumen of the tubular frame, extending from a near-proximal location to a near-distal location. The liner is attached to the frame at at least one end, as well as at a plurality of locations between said ends. Optionally, a second liner may be provided over at least a portion of the exterior of the frame to cover both sides of the frame. Such exterior coverage provides a circumferential seal against the inner wall of the blood vessel lumen in order to inhibit leakage of blood flow between the graft and the luminal wall into the aneurysm or stenosis which is being treated.

The grafts of the present invention will find particular use in the treatment of vascular conditions, such as abdominal and other aneurysms, vascular stenoses, and other conditions which require creation of an artificial vessel lumen. For the treatment of vascular stenoses, the graft may serve as a stent to maintain vessel patency in a manner similar to that described in the above-described U.S. and foreign patent documents relating to stents. Other intraluminal uses of the devices and methods of the present invention include stenting of the ureter, urethra, biliary tract, and the like. The devices and methods may also be used for the creation of temporary or long term lumens, such as the formation of a fistula.

Such graft structures provide a number of advantages over previously proposed designs, particularly for vascular uses. By covering the lumen of the tubular frame, thrombogenicity of the graft resulting from exposed frame elements is greatly reduced or eliminated. Such reduction of thrombogenicity is achieved while maintaining the benefits of having a frame structure extending over the graft. Such an external frame helps anchor the graft in place and maintain patency and evenness of the graft lumen, both of which are advantages over graft structures which are anchored and supported only at each end. The vascular grafts of the present invention are also self-expanding and easy to place. The self-expanding nature of the frame also counteracts external deforming forces that may result from the continuous physiologic expansion and contraction of the blood vessel lumen. Moreover, the lack of cleats, tines, or other penetrating elements on the graft allows the graft to more closely conform to the surrounding vessel wall and facilitates retrieval and/or repositioning of the graft, as will be described in more detail hereinafter. Additionally, the resilient tubular frame structure permits the graft to conform to even irregular regions of the blood vessel wall as the wall is expanding and contracting as a result of the pumping of the patient's heart.

The tubular frame preferably comprises a plurality of radially compressible band or ring structures, each of which have a relaxed (i.e., non-compressed) diameter which is greater than the diameter of the blood vessel to be treated. Adjacent compressible band members may be independent of each other or may be joined at one or more locations therebetween. If joined, the bands are preferably joined at only two diametrically opposed points to enhance flexibility of the frame over its length. Independent band members will be held together by their attachment to the interior and/or exterior liner(s).

Alternatively, the tubular frame may comprise a plurality of laterally compressible axial members, with adjacent axial members preferably not being directly connected to each other. The axial members will usually comprise a multiplicity of repeating structural units, e.g., diamond-shaped elements, which are axially connected. The axial members will be attached to the inner liner, either by stitching or by capturing the axial members in pockets formed between the inner liner and an outer liner disposed over the frame. The pockets may be formed by attaching the inner and outer liners to each other along axial lines between adjacent axial members.

The present invention also provides methods and systems for the in situ placement of bifurcated grafts for the treatment of aorto-iliac segments and other bifurcated lumens. The system comprises a bifurcated base structure including a proximal anchor, typically a self-expanding frame, which defines a common flow lumen and a pair of connector legs that establish divergent flow lumens from the common flow lumen. The system also includes a first tubular graft which can be anchored within first of the connector legs to form a continuous extension of the first divergent flow lumen and a second tubular graft which can be anchored within a second of the connector legs to form a continuous extension of the second divergent flow lumen. The method of placement comprises first introducing the bifurcated base structure so that the anchor section is positioned within a primary vessel, i.e., the aorta, below the renal arteries. After the bifurcated base structure is anchored, the first tubular graft is introduced into the first connector leg and anchored between said leg and the first branch artery, e.g., the right iliac. The second tubular graft is then inserted into the second connector section and anchored between the second connector and the second branch artery. By properly selecting the dimensions of the bifurcated base structure, the first tubular graft, and the second tubular graft, the resulting bifurcated graft structure can have dimensions which are specifically matched to the vessel dimensions being treated. Preferably, the bifurcated base structure, first tubular graft, and second tubular graft, will be formed from radially compressible perforate tubular frames having interior and/or exterior liners, generally as described above for the preferred vascular graft of the present invention. The radially compressible perforate tubular frame on the base structure, however, will terminate above the region where the connector legs diverge. The connector legs below the divergent region will be reinforced by placement and expansion of the tubular graft structures therein.

The present invention further provides a delivery catheter for endovascular placement of radially compressible grafts or stents, such as the vascular grafts and bifurcated base structures described above. The catheter comprises an elongate shaft having a proximal end and a distal end. Preferably, a retaining structure is provided near the distal end of the shaft for holding the graft or the stent on the shaft until such a time that the graft or stent is positively released, e.g., by withdrawing a pull wire which extends through locking stays on either side of the graft or stent. The delivery catheter further comprises a sheath slidably mounted over the shaft. The sheath is initially disposed to cover and restrain the radially compressed graft or stent while the catheter is being intervascularly introduced to a desired target location. The sheath may then be withdrawn, releasing the radially compressed graft or stent to occupy and anchor within the vasculature or other body lumen.

Preferably, the graft or stent will remain fixed to the shaft even while the sheath is being withdrawn so that the physician can recapture the graft by advancing the sheath back over its exterior. Only after the graft or stent is fully expanded at the target location within the vessel lumen is the graft or stent finally released. Preferably, the sheath will have a flared or outwardly tapered distal end to facilitate both release and recapture of the graft or stent by axial translation of the sheath. The flared end may be fixed or deployable, i.e., selectively shiftable between a flared and a non-flared configuration. Preferably, the flared end will be deployable so that the sheath may be introduced with the distal end in its non-flared configuration to minimize its profile. After properly positioning the sheath, the distal end may be opened to assume its tapered configuration.

BRIEF DESCRIPTION OF THE DRAWINGS

FIG. 1B is a side view of a second alternate embodiment of a vascular graft constructed in accordance with the principles of the present invention.

DESCRIPTION OF THE SPECIFIC EMBODIMENT

Figure 1:
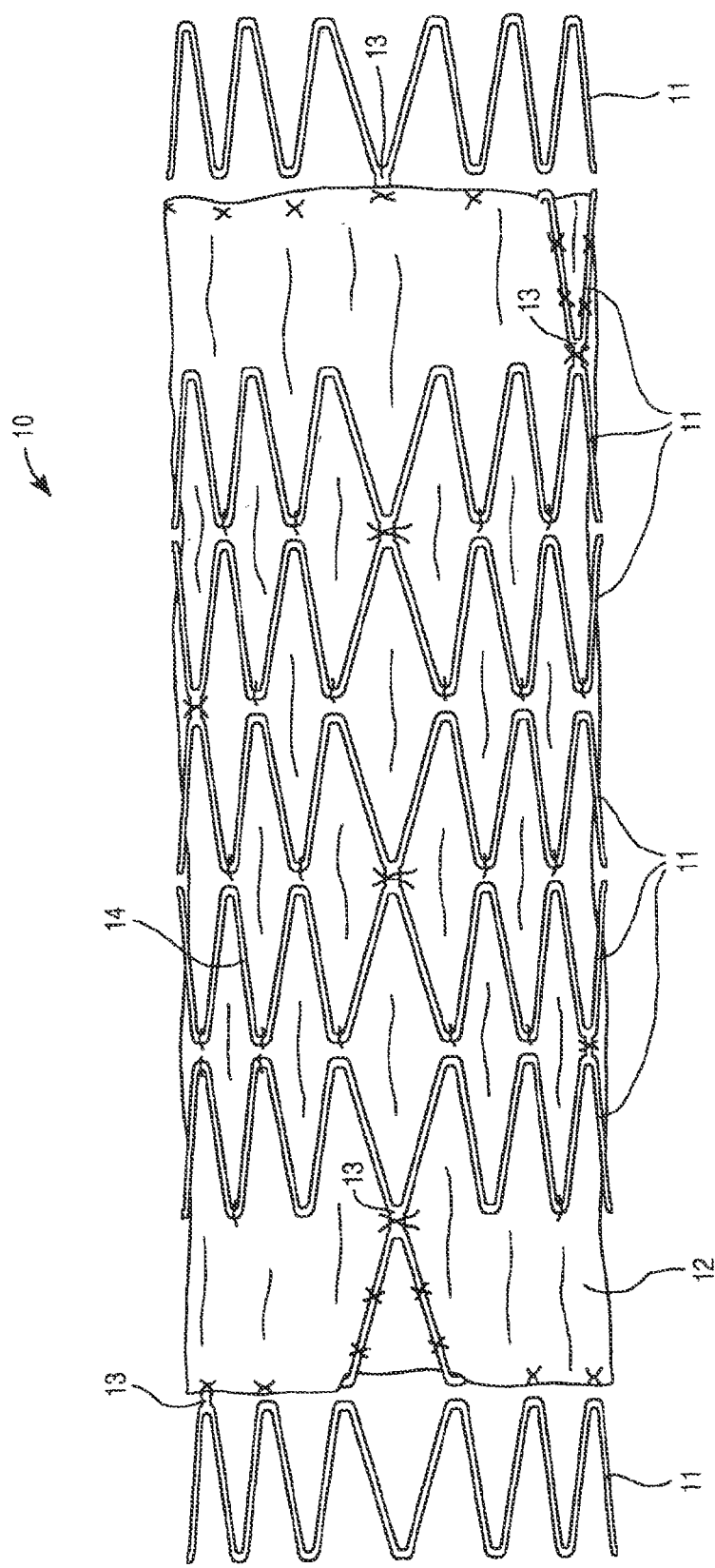
FIG. 1 is a side view of a vascular graft constructed in accordance with the principles of the present invention.

The present invention provides apparatus and methods for the transluminal placement of graft structures, particularly within the vascular system for treatment of aneurysms and other vascular conditions, but also in other body lumens, such as ureter, urethra, biliary tract, gastrointestinal tract, and the like, for the treatment of other conditions which benefit from the introduction of a reinforcing or protective structure in the lumen. The apparatus and methods can also find use in the creation of artificial lumens through solid tissue and structures, such as the placement of a TE fistula via an endoscope. The vascular grafts will be placed endovascularly. As used herein, "endovascularly" will mean placement by percutaneous or cutdown transluminal procedures using a catheter over a guidewire under fluoroscopic guidance. The catheters and guidewires may be introduced through conventional access sites to the vascular system, such as through the brachial and subclavian arteries for access to the aorta and through the femoral arteries for access to the aorta or to peripheral and branch blood vessels.

A vascular graft according to the present invention will comprise a radially compressible perforate tubular frame and an inner or interior liner attached within a central lumen defined by the frame and optionally a second or outer liner formed over the exterior of the frame. The radially compressible frame can take a variety of forms, usually comprising or consisting of a plurality of independent or interconnected structural elements, such as rings, bands, helical elements, serpentine elements, axial struts, parallel bars, and the like, that can be compressed from a relaxed, large diameter configuration to a small diameter configuration to facilitate introduction, as discussed below. It is necessary, of course, that the liner(s) remain attached to the frame both in its radially compressed configuration and in its expanded, relaxed configuration.

A preferred configuration for the tubular frame comprises a plurality of radially compressible band members, where adjacent band members are joined to each other at only two diametrically opposed points in order to enhance flexibility. In a particularly preferred aspect, the diametrically opposed attachment points are rotationally staggered in order to provide flexibility in more than one direction. A preferred method for forming such a tubular frame is described in more detail hereinafter. In another preferred configuration, at least some of the bands of the frame are independent i.e., are not directly connected to each other. Instead, the bands are connected only to the liner(s) which maintain the axial integrity of the graft. Preferably, the independent bands are stitched or sealed between interior and exterior liners, as will be described in more detail below. Other suitable frame structures are described in the patent literature.

In an alternate configuration, the perforate tubular frame comprises a plurality of laterally compressible axial members which are attached directly, e.g., by stitching, or indirectly, e.g., by lamination, to the inner liner. The axial members may be a multiplicity of repeating structural elements, such as diamonds, or could be formed from two or more overlapping elements. By positioning the axial members in pockets formed between an inner liner and an outer liner, the axial elements will be able to flex independently while providing the desired radial compressibility and self-expansion characteristics for the graft.

The dimensions of the tubular graft will depend on the intended use. Typically, the graft will have a length in the range from about 50 mm to 500 mm, preferably from about 80 mm to 200 mm for vascular applications. The relaxed diameter will usually be in the range from about 4 mm to 45 mm, preferably being in the range from about 5 mm to 25 mm for vascular applications. The graft will be radially compressible to a diameter in the range from 3 mm to 9 mm, preferably from 4 mm to 6 mm for vascular applications.

The liner(s) will be composed of conventional biological graft materials, such as polyesters, polytetrafluoroethylenes (PTFE's), polyurethanes, and the like, usually being in the form of woven fabrics, non-woven fabrics, polymeric sheets, membranes, and the like. A presently preferred fabric liner material is a plain woven polyester, such as type 56 Dacron® yarn (Dupont, Wilmington, Del.), having a weight of 40 denier, woven at 27 filaments with 178 warp yarns per circumferential inch, and 78 yarns per inch in the fill direction.

The liner will be attached to the interior lumen of the tubular frame and will cover most or all of the interior surface of the lumen. For example, the liner may be stitched or otherwise secured to the tubular frame along a plurality of circumferentially spaced-apart axial lines. Such attachment permits the liner to fold along a plurality of axial fold lines when the frame is radially compressed. The liner will further be able to open and conform to the luminal wall of the tubular frame as the frame expands. Alternatively, when inner and outer liners are used, the liners may be stitched, heat welded, or ultrasonically welded together to sandwich the tubular frame therebetween. In an exemplary embodiment where a plurality of independent band members are disposed between interior and exterior liners, the liners are secured together along circumferential lines between adjacent band members to form pockets for holding the band members. In a second exemplary embodiment where a plurality of independent axial members are disposed between interior and exterior liners, the liners are secured together along axial lines to form pockets for holding the axial members.

The liner will preferably be circumferentially sealed against the tubular frame at least one end, preferably at both ends in the case of straight (non-bifurcated) grafts. It is also preferred in some cases that the distal and proximal end of the perforate tubular frame be exposed, i.e., not covered by the liner material, typically over a length in the range from about 1 mm to 25 mm. Frame which is not covered by the liner permits blood perfusion through the perforations and into branch arteries such as the renal arteries in the case of abdominal aorta grafts, while providing additional area for anchoring the frame against the blood vessel lumen. In an exemplary embodiment, the liner will extend through the frame and over the exterior surface near either or both ends to provide a more effective seal against the adjacent blood vessel wall.

The radially compressible perforate tubular frame will be composed of a resilient material, usually metal, often times a heat and/or shape memory alloy, such as nickel titanium alloys which are commercially available under the trade name Nitinol®. The frames may also be composed of other highly elastic metals, such as MP-35 N, Elgiloy, 316 L stainless steel, and the like. In the case of Nitinol® and other memory alloys, the phase transition between austenitic and martensitic states may occur between an introduction temperature, e.g., room temperature (approximately 22° C.), and body temperature (37° C.), to minimize stress on the unexpanded frame and enhance radial expansion of the frame from its radially compressed condition. Expansion can also be achieved based on the highly elastic nature of the alloy, rather than true shape recovery based on phase change.

In some cases, it may be desirable to form a tubular frame having different elastic or other mechanical properties at different regions along its length. For example, it is possible to heat treat different regions of the tubular frame so that some regions possess elastic properties while others become malleable so that they may be deformed by external force. For example, by providing at least one malleable end portion and an elastic (radially compressible) middle portion, the graft can be firmly expanded and implanted by internal balloon expansion force (to anchor the end(s) in the inner wall of the blood vessel) while the middle will remain open due to the elastic nature of the tubular member. Malleable end portions are a particular advantage since they can be expanded with a sufficient force, and re-expanded if necessary, to assure a good seal with the blood vessel wall. Alternatively, the malleable ends could be formed from a different material than that of the middle portion of the tubular frame. The use of different materials would be particularly convenient when the frame is formed from a plurality of independent bands, where one or more band members at either or both ends could be formed of a malleable metal. Usually, such malleable end(s) will extend over a distance in the range from 5 mm to 50 mm, preferably from 5 mm to 20 mm.

Malleable portions or segments can also be formed in other parts of the tubular frame. For example, some circumferentially spaced-apart segments of the tubular frame could be malleable while the remaining circumferential segments would be elastic. The frame would thus remain elastic but have an added malleability to permit expansion by applying an internal expansion force. Such a construction would be advantageous since it would allow the diameter of the graft or stent structure to be expanded if the initial diameter (which resulted entirely from elastic expansion) were not large enough for any reason. The proportion of elastic material to malleable material in the tubular frame can be selected to provide a desired balance between the extend of initial, elastic opening and the availability of additional, malleable opening. Such construction can be achieved by selective heat treatment of portions of a frame composed of a single alloy material, e.g. nickel titanium alloy, or by forming circumferential segments of the frame from different materials having different elastic/malleable properties. In particular, individual laterally compressible axial members 204 (as described in connection with FIG. 1B) could be formed from materials having different elastic/malleable properties.

Referring now to FIGS. 1-4, an exemplary graft structure 10 will be described. The graft structure 10 includes a fabric liner 12 and a radially compressible perforate tubular frame 14. For convenience, the frame 14 is illustrated by itself in FIG. 2. The frame is illustrated in its expanded (relaxed) configuration in each of these figures, but may be radially compressed by applying a radially inward compressive force, usually by placing the graft 10 in an outer sheath, as will be described in more detail hereinafter.

The tubular frame 14 comprises a plurality of radially compressible band members 11, each of which comprises a zig-zag or Z-shaped element which forms a continuous circular ring. Each band member 11 will typically have a width w in the range from 2 mm to 15 mm, and the tubular frame will comprise from 1 to 30 individual band members. Adjacent band members 11 are preferably spaced-apart from each other by a short distance d and are joined by bridge elements 13. Flexibility is enhanced by providing only two diametrically opposed bridge elements 13 between each adjacent pair of band members 11. As will be described further with reference to FIG. 1A, flexibility can be further enhanced by leaving the band members connected only by the liner.

Usually, the perforate tubular frame 14 will be left open at each end, e.g., at least a portion of the last band member 11 will remain uncovered by the liner 12. The liner 12 will be stitched or otherwise secured to the band members 11, preferably at the junctions or nodes when the element reverses direction to form the Z-pattern (although the stitching should not cross over between the band members in a way that would restrict flexibility). The liner 12 will usually pass outward from the inner lumen of the tubular frame 14 to the exterior of the frame through the gap between adjacent band members, as illustrated in FIG. 1. The portion of liner 12 on the exterior of the tubular frame 14 helps seal the end(s) of the graft 10 against the wall of the blood vessel or other body lumen in which it is disposed.

Figure 3A:
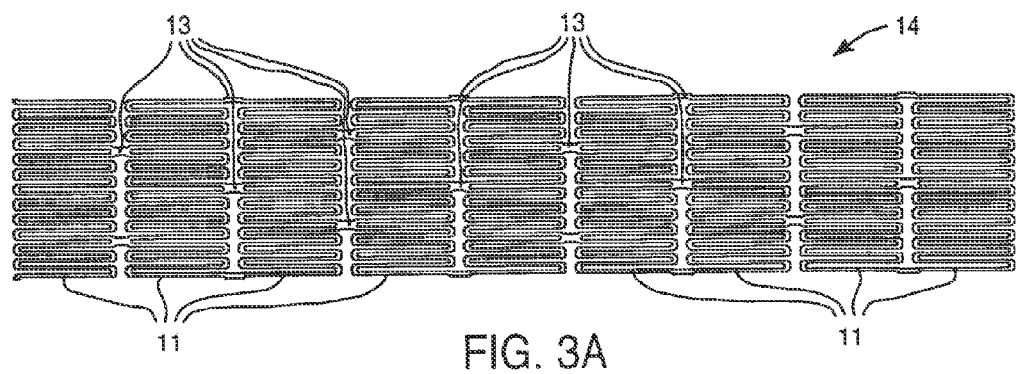
FIGS. 3A and 3B are a schematic illustrations showing the joining pattern of the radially compressible band members of the tubular frame of FIG. 2.
Figure 3B:
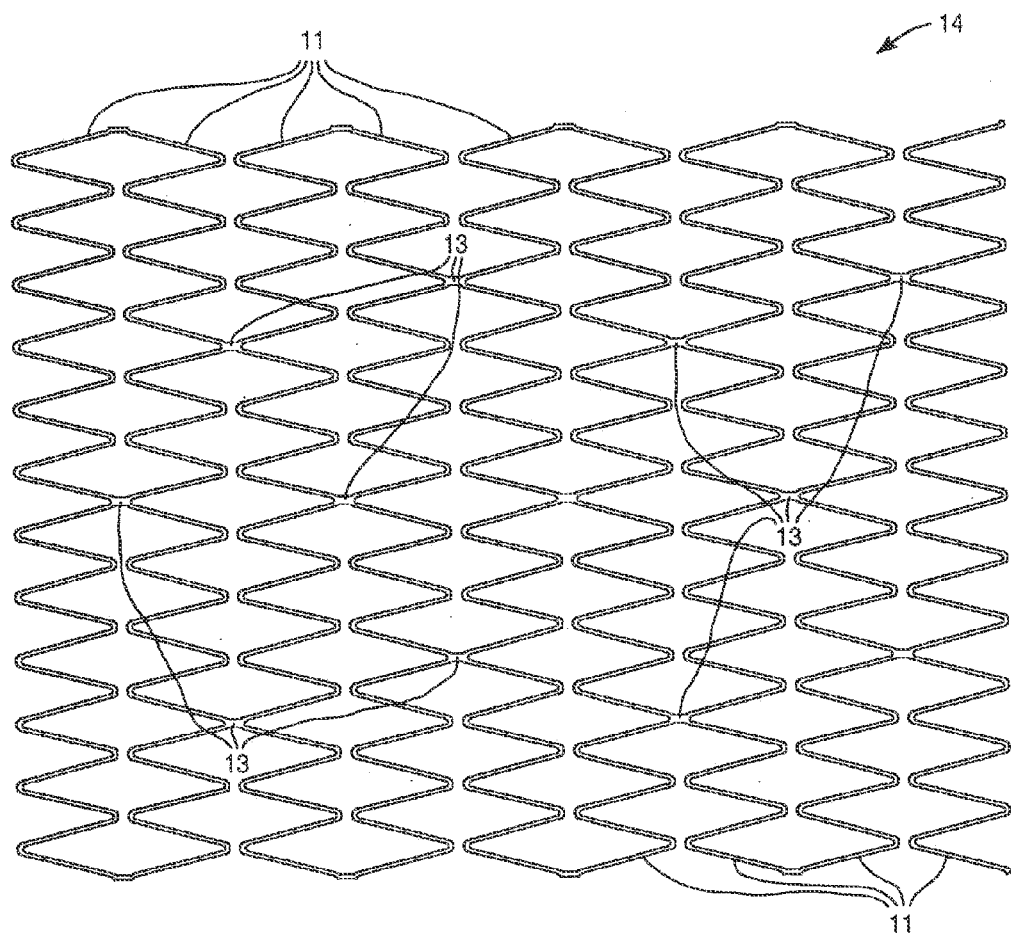

The joining pattern of adjacent band members 11 is best illustrated in FIGS. 3A and 3B. FIG. 3A illustrates the tubular frame 14 as it would look if unrolled onto a flat surface. FIG. 3B is similar to FIG. 3A, except that the band members are expanded. The expansion is shown at 30°, but will frequently extend up to 60° or higher in use.

Figure 4:
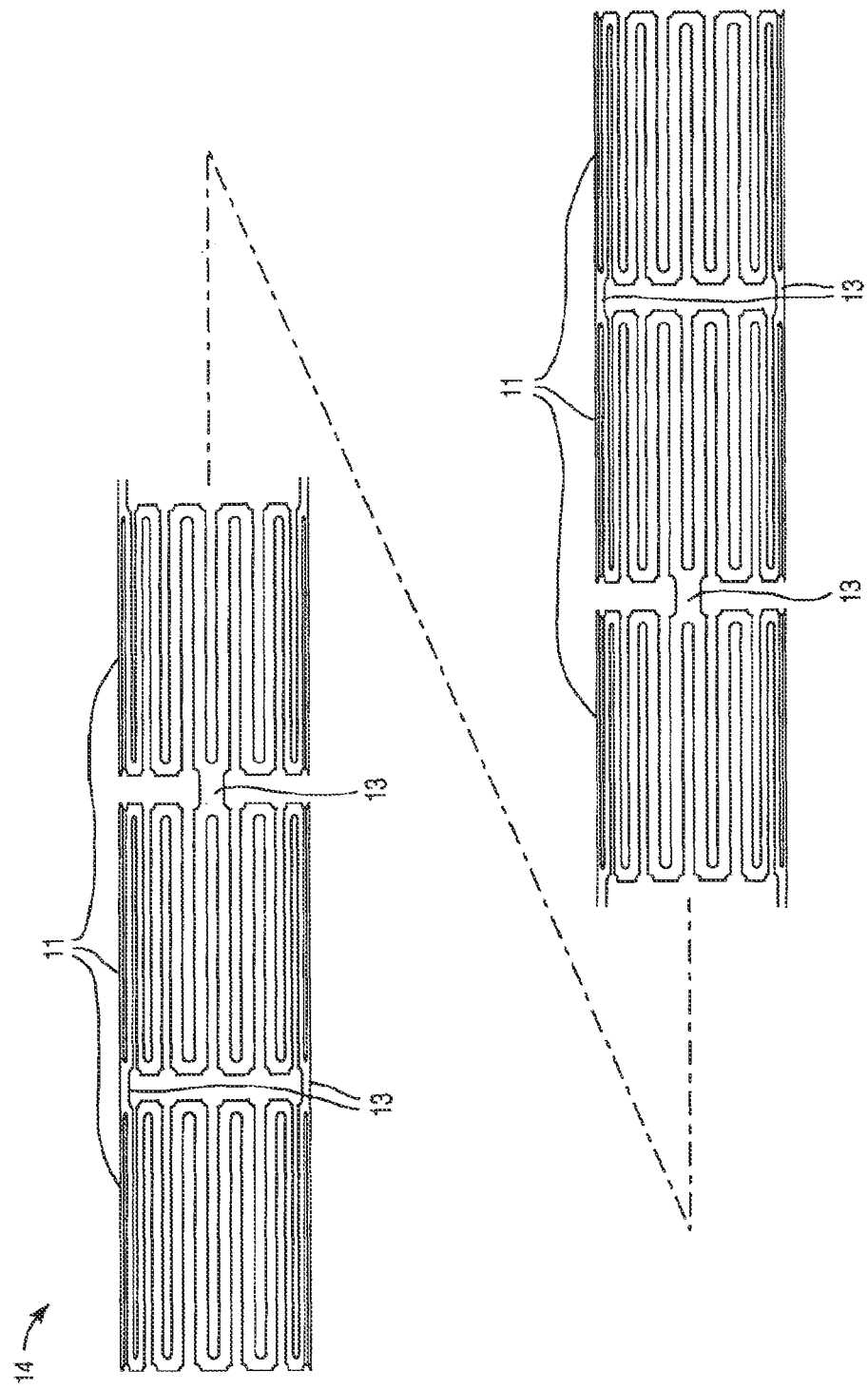
FIG. 4 illustrates a structure which has been etched from a tube and which may be subsequently expanded to form the tubular frame of FIG. 2.

A preferred method for forming the tubular frame 14 in the present invention may be described with reference to FIG. 4. A tube of the desired elastic material, such as nickel titanium alloy having a phase transformation temperature significantly below 37° C., preferably between 30° C. and 32° C., is obtained. The tube will have dimensions roughly equal to the desired dimensions of the frame when radially compressed. The tube may be drawn, rolled, or otherwise treated to achieve the desired wall thickness, diameter, and the like. Suitable wall thicknesses are in the range of about 0.1 mm to 0.5 mm. A pattern of axial slots is then formed in the tube, as illustrated in FIG. 4. The slots may be formed by electrical discharge machining (EDM), photochemical etching, laser cutting, machining or other conventional techniques. After the slots have been formed, the tube is mechanically expanded to its desired final (relaxed) diameter and heat treated at a suitable temperature to set the tube in the desired expanded state. Sharp edges are removed by conventional techniques, such as deburring, abrasive extrusion, or the like. The result of the expansion is the tubular frame illustrated in FIGS. 1 and 2.

Figure 1A:
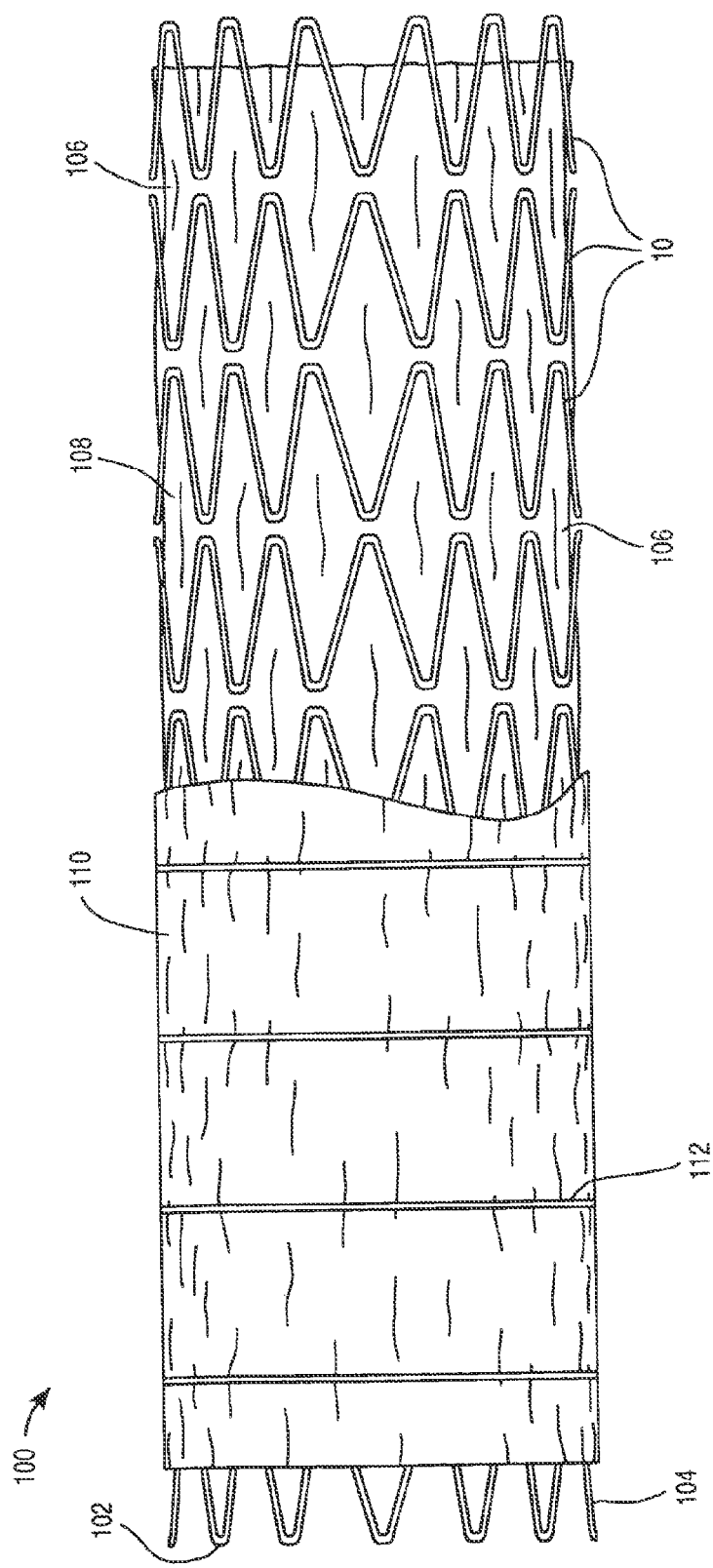
FIG. 1A is a side view of a first alternate embodiment of a vascular graft constructed in accordance with the principles of the present invention.
Figure 2:
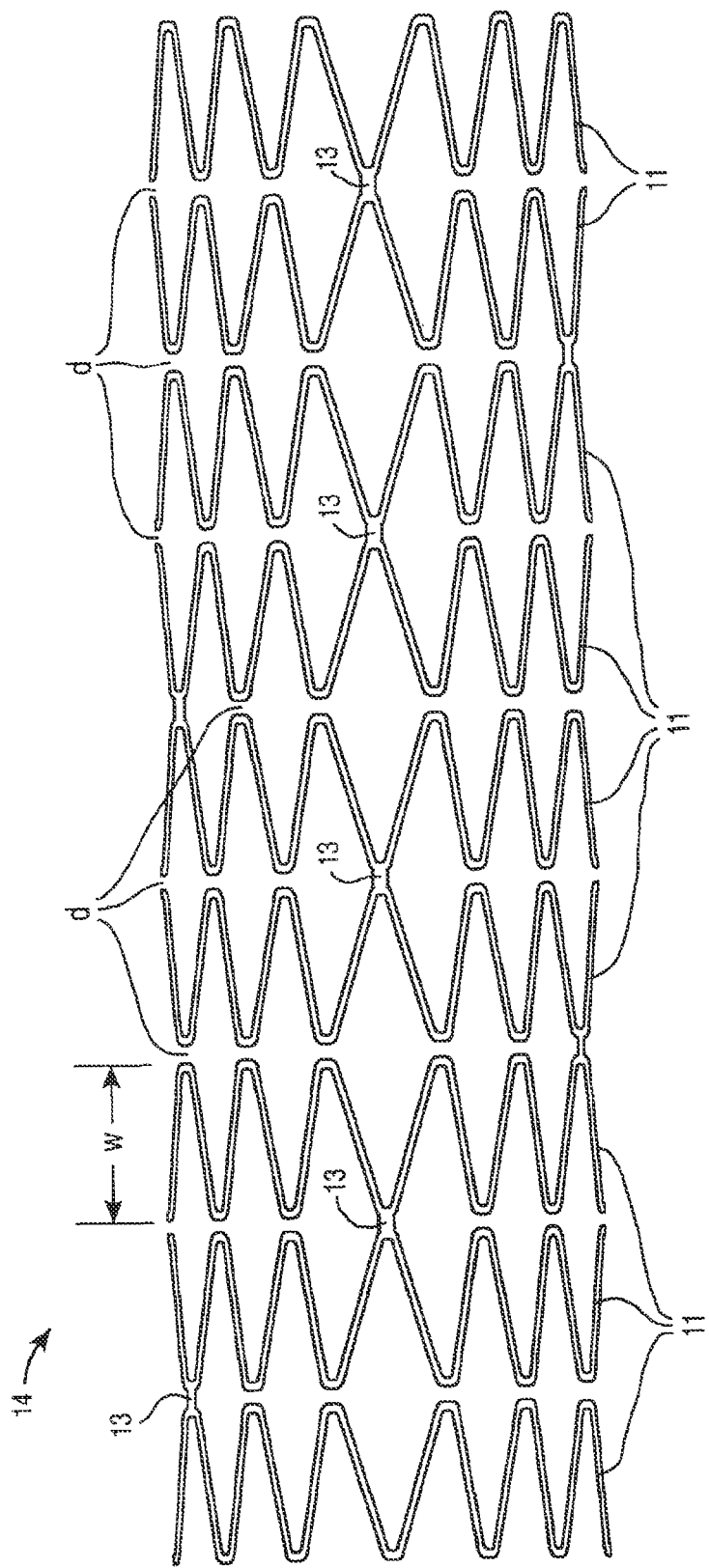
FIG. 2 is a side view of a radially compressible perforate tubular frame of a type which may be used in a vascular graft of FIG. 1.

Preferably, each end of the liner 12 will be circumferentially sealed at or near the distal and proximal ends of the tubular graft. As illustrated in FIG. 1A, this can be achieved by folding over the end of the liner 12 onto the external surface of the graft 10. Conveniently, this can be done through the gaps which are present between adjacent band members 14. Where the junctions 13 remain, the liner 12 can be carefully stitched onto the underlying surface of the frame, as shown at 18 in FIG. 1A. Other techniques for circumferentially sealing the liner include heat or ultrasonic welding of the liner, laminating an outer gasket, sewing an outer reinforcement member, or the like.

Referring now to FIG. 1A, an alternative embodiment 100 of a vascular graft constructed in accordance with the principles of the present invention will be described. The graft 100 comprises a perforate tubular frame 102 which includes a plurality of independent (non-connected) band members 104 separated from each other by gaps 106. The perforate tubular frame 102 is similar in construction to frame 14 of graft 10, except that adjacent band members 104 are not directly connected to each other. Band numbers 104 will be connected only by an inner liner 108 and an outer liner 110, where the inner and outer liners together encase or sandwich the otherwise free-floating band members 104. In order to secure the band members 104 in place, and secure the liners to the perforate tubular frame 102, the inner and outer liners are joined together along circumferential lines 112, preferably located in the gaps 106 between adjacent band members 104. The liners may be joined together by stitching, heat welding, ultrasonic welding, or the like. In the exemplary embodiment, the liners 108 and 110 are formed from polymeric sheet material and are joined together by ultrasonic welding. The band members 104 at each end of the graft 100 will have to be further secured to the liners 108 and 110. For example, they could be stitched, welded, or otherwise joined to the liners to hold them in place. The dimensions, materials, and other aspects of the graft 100 will be generally the same as those described previously for graft 10.

Referring now to FIG. 1B, a second alternative embodiment 200 of the vascular graft of the present invention is illustrated. The graft 200 comprises a perforate tubular frame 202 including a plurality of laterally compressible axial members 204. Each axial member 204 comprises a plurality of diamond-shaped structural elements which are connected to each other in a linear fashion. It will be appreciated that each diamond-shaped structural element is laterally compressible so that the frame 202 as a whole may be radially compressed from a reduced-diameter configuration to an expanded-diameter configuration. As illustrated in FIG. 1B, the frame is in a partially compressed configuration. The axial members 202 will be captured between an inner liner 206 and an outer liner 208. The inner liner 206 and outer liner 208 will be secured to each other along a plurality of axial lines 210 disposed between adjacent axial members 204. In this way, each axial member 204 will be captured within a pocket formed between the inner liner 206 and outer liner 208. As with previous embodiments, the ends of the frame may extend beyond the liners to provide for improved anchoring and perfusion on either side of the graft.

Figure 5:
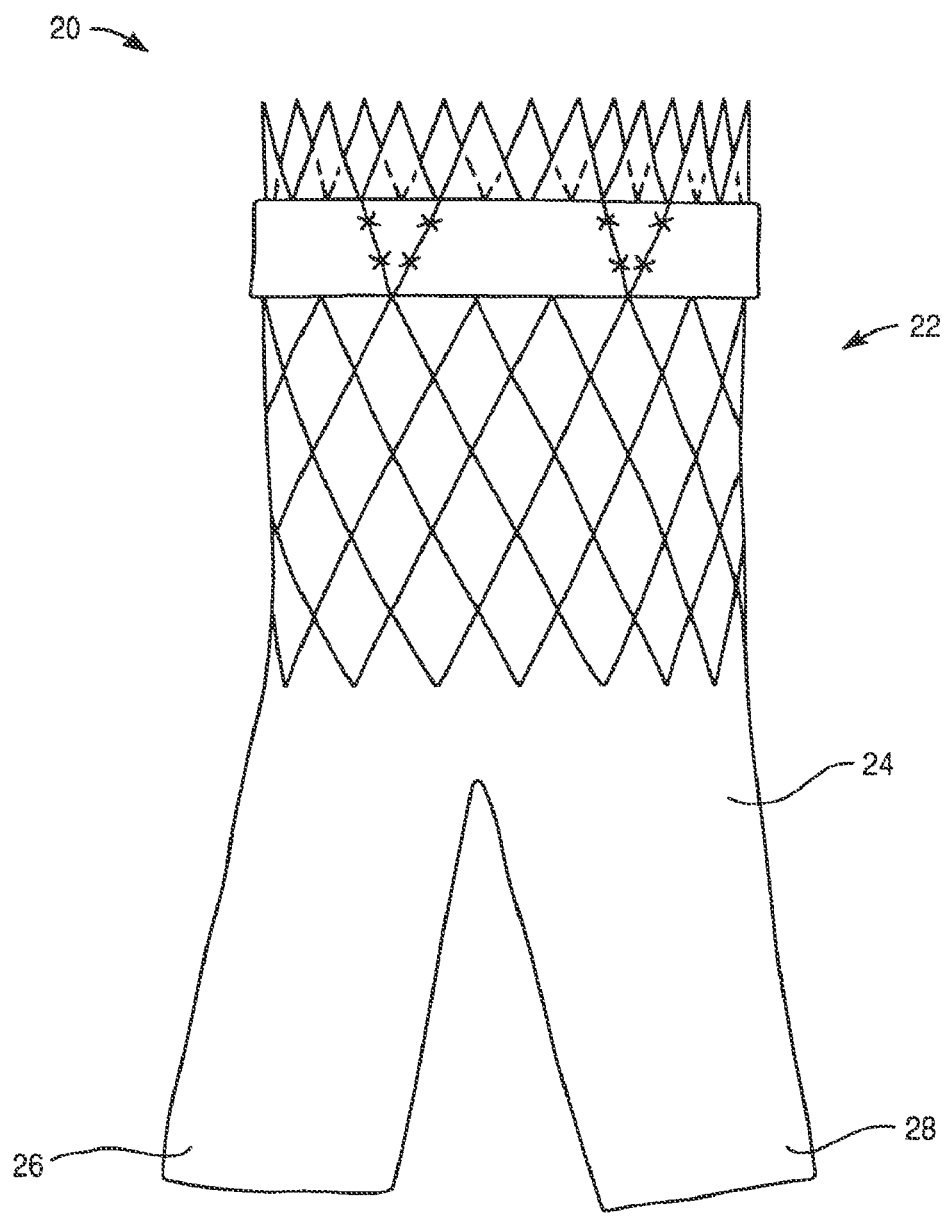
FIG. 5 illustrates a bifurcated base structure which is part of a system for forming a bifurcated graft in situ.

Referring now to FIG. 5, a bifurcated base structure for forming a bifurcated graft in combination with a pair of the vascular grafts 10 just discussed will be described. The bifurcated base structure 20 comprises an anchor segment 22, which typically will be a radially compressible perforate frame having a structure similar or identical to that just discussed. The frame of anchor 22 will typically have a length in the range from about 5 mm to 50 mm, and a diameter in the range from about 5 mm to 30 mm. A liner 24 will be disposed within the frame 22, typically being circumferentially sealed near the upper end of the frame, e.g., being folded over and stitched as described previously. As with the straight graft embodiment of FIGS. 1-4, the proximal end of the liner 24 will preferably be distally spaced-apart from the proximal end of the anchor segment 22, typically by a distance in the range from 1 mm to 25 mm. The fabric 24 defines a common flow lumen at its upper end and a pair of divergent flow lumens at its lower end, one in each leg 26 and 28. The legs 26 and 28 are preferably not covered by the frame of anchor 22. The fabric legs 26 and 28 will each have a diameter in the range from 6 mm to 18 mm and a length in the range from 5 mm to 30 mm. The dimensions of each leg need not be the same.

Figure 6:
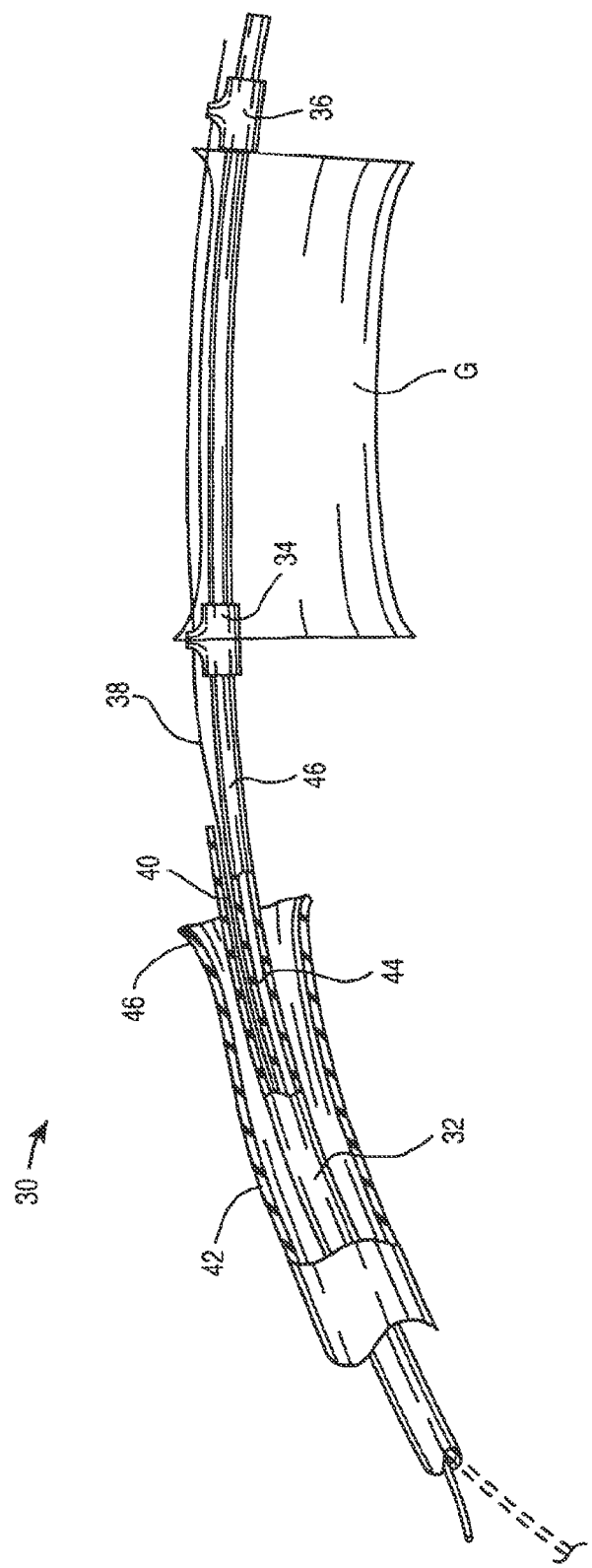
FIG. 6 illustrates, the distal end of a graft and stent placement catheter constructed in accordance with the principles of the present invention.

Referring to FIG. 6, a catheter 30 for delivering the vascular graft 10 or bifurcated base structure 20 will be described. The catheter 30 includes a shaft 32 having a pair of axially spaced-apart stays 34 and 36. A pull wire 38 extends through a lumen 40 of shaft 32 and through protrusions on each of the stays 34 and 36. A sheath 42 is slidably disposed over the shaft 32 so that it may be advanced over the stays 34 and 36. Guidewire GW extends through the shaft 32 within guidewire lumen 44 and shaft extension 46 to facilitate vascular introduction of the catheter 30. A radially compressible graft G (such as graft 10) is placed over the distal end of the shaft extension 46, generally being aligned between the stays 34 and 36. The pull wire 38 is then advanced through the stays 34 and 36 so that it passes through each end of the graft G to maintain the graft in place until the pull wire is withdrawn. While the pull wire 38 remains in place, the sheath 42 may be axially advanced over the graft to radially compress the graft into its desired low profile diameter. The sheath 42 includes a flared (i.e., outwardly tapered) distal end 56 to facilitate advancing the sheath over the graft, in particular so that the graft may be recaptured when it is partially deployed, as described hereinafter. The outward taper may be permanently fixed in the body of the sheath, but will preferably be selectively deployable between the tapered configuration and a non-tapered or straight configuration (shown in broken line) to facilitate introduction of the sheath through the vasculature or other body lumen. A variety of suitable mechanisms for selectively expanding the distal end of the sheath are known in the art, such as pull wires and the like. The sheath 42 will be introduced through the vasculature through a conventional introducer sleeve having a proximal hemostasis valve.

The catheter 30 may be modified to provide alternate delivery techniques for the graft G. For example, the catheter 30 may include a balloon at or near its distal end for use with grafts having malleable portions which need to be expanded. The catheter 30 might also include bumpers or other means for aligning the graft on the shaft 46 while the sheath 42 is being retracted. A variety of other catheter constructions and techniques for delivering the radially-compressible graft and stent structures of the present invention.

Figure 7:
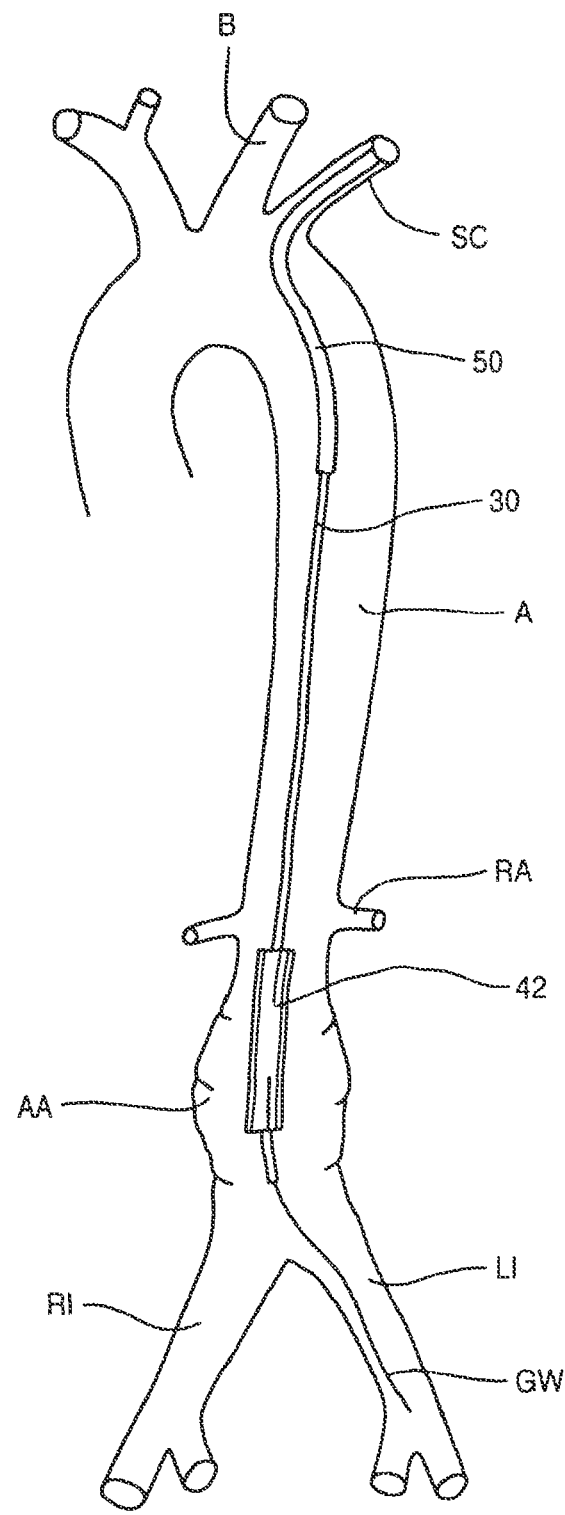
FIGS. 7-12 illustrate placement of a bifurcated aortic graft using the bifurcated graft placement system of the present invention.
Figure 8:
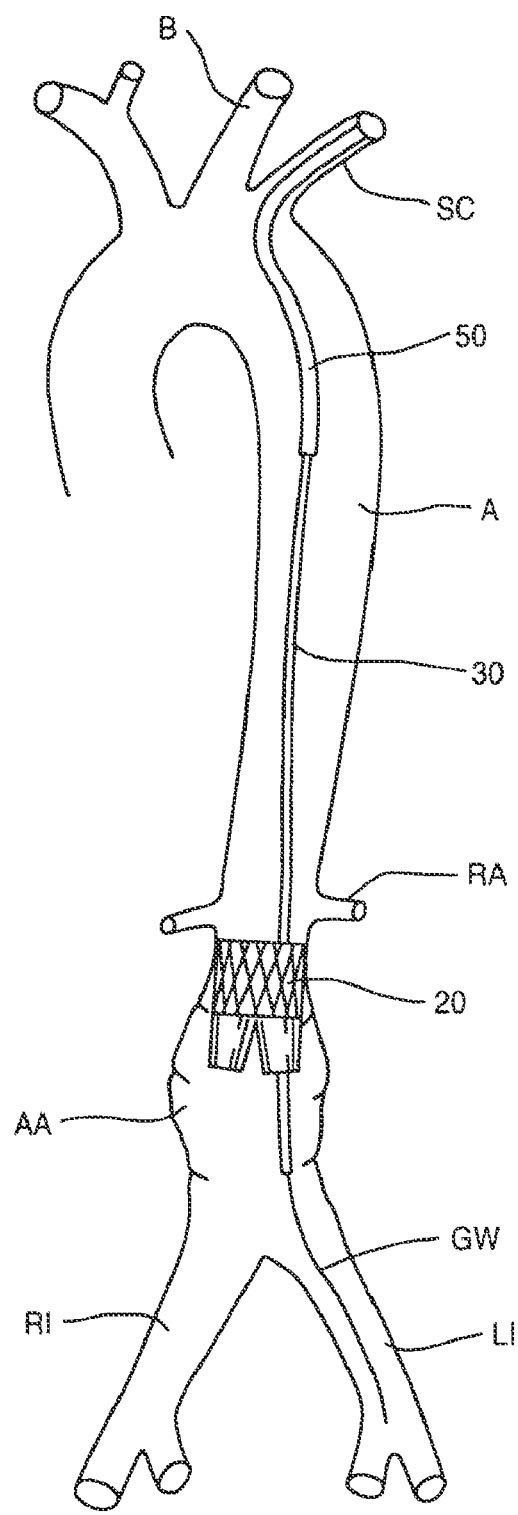
Figure 9:
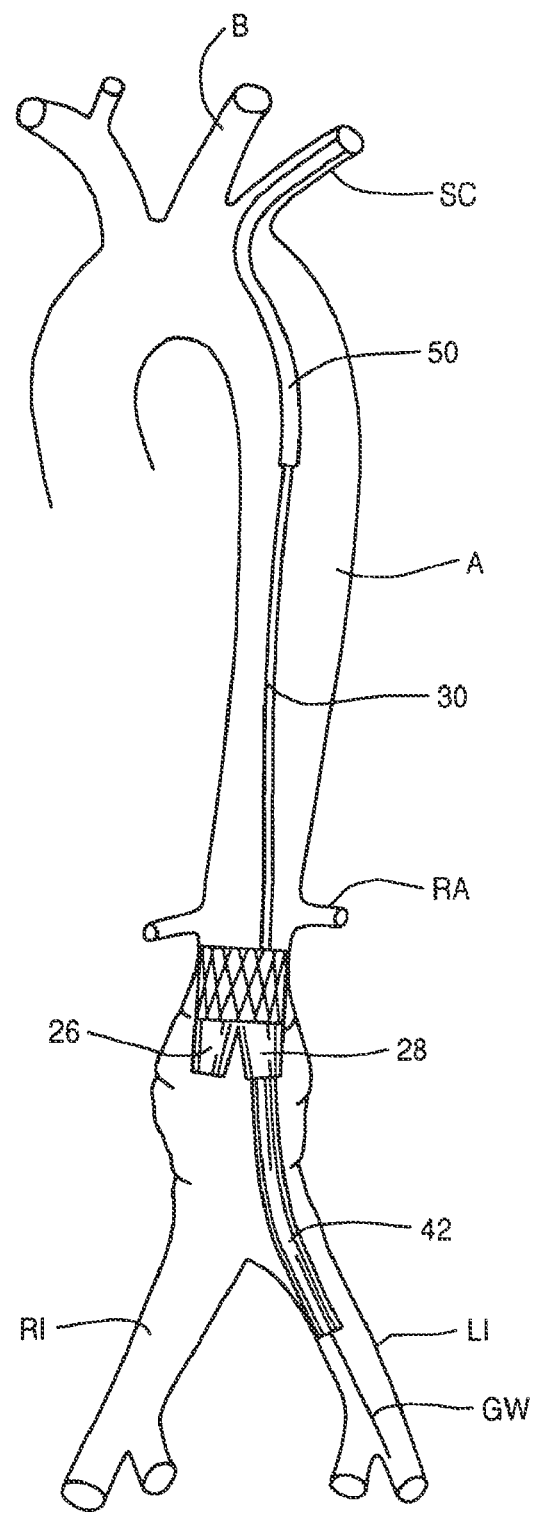
Figure 10:
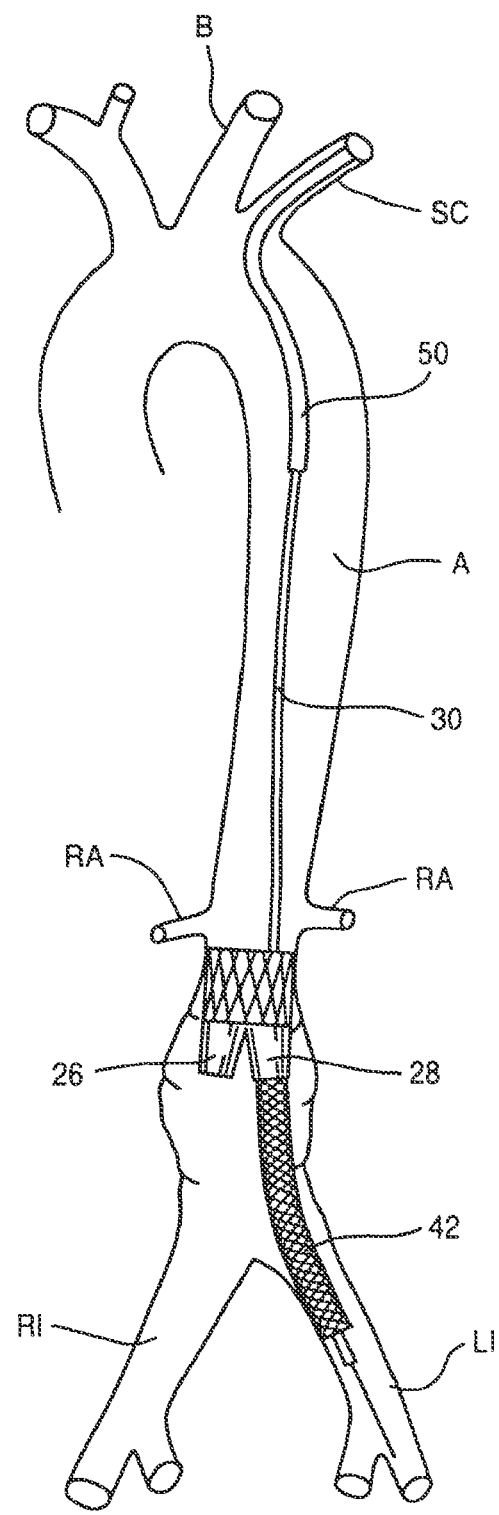
Figure 11:
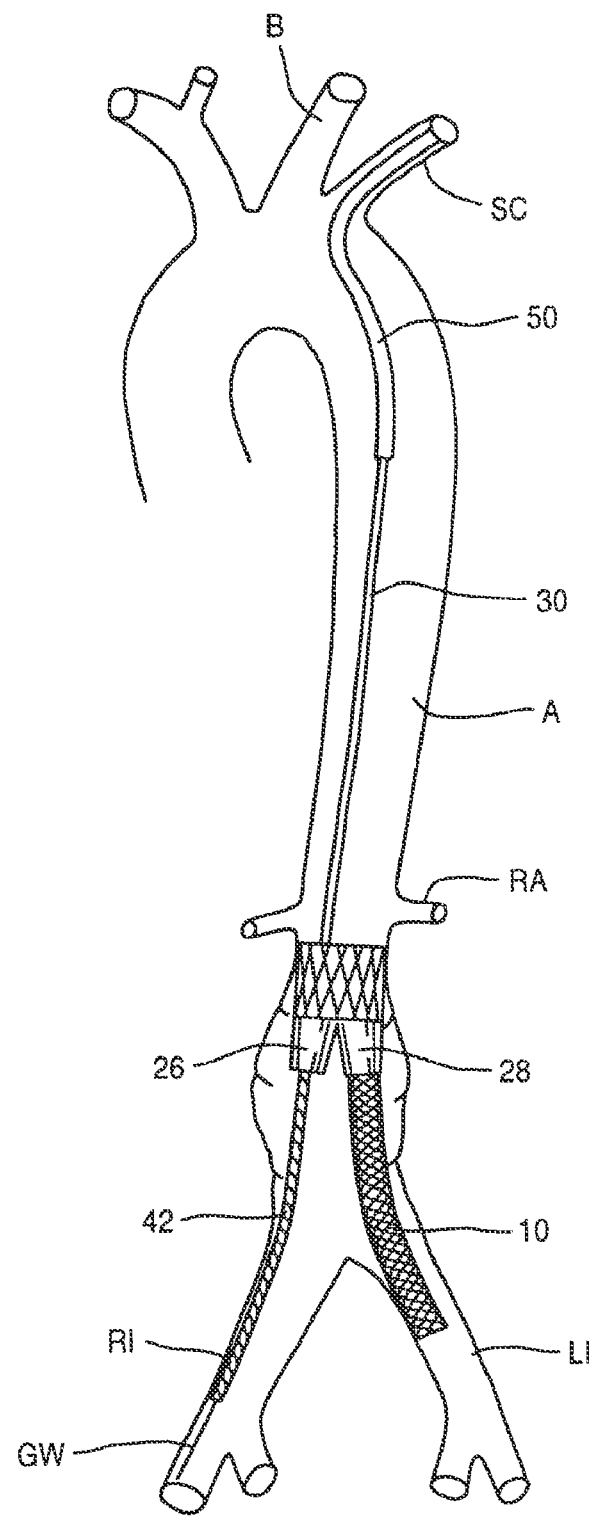
Figure 12:
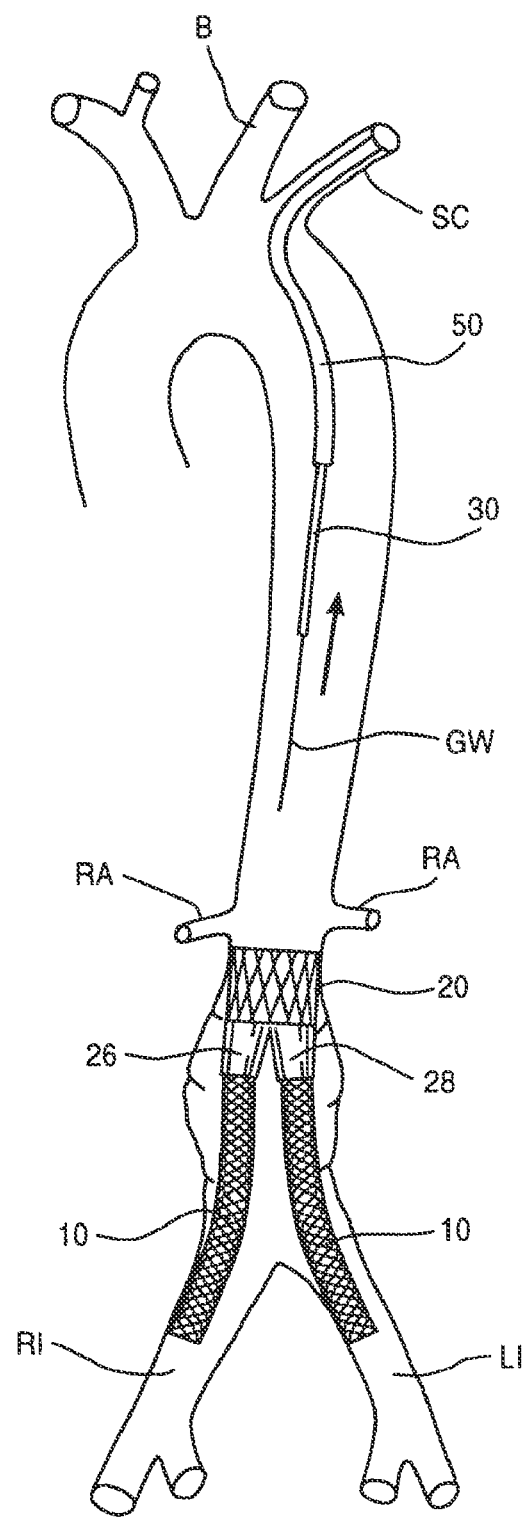

Referring now to FIGS. 7-12, placement of a bifurcated graft structure in an abdominal aortic aneurysm AA of a patient will be described. Initially, the delivery catheter 30 is introduced through an introducer sleeve 50 via an antegrade approach (e.g. the subclavian artery SC), as illustrated in FIG. 7. The bifurcated base structure is initially maintained within sheath 42 so that it remains radially compressed. After the compressed base structure 20 is properly positioned, the sheath 42 will be withdrawn, allowing the base structure 20 to expand in place, as illustrated in FIG. 8. The catheter 30 may then be withdrawn, leaving the guidewire GW in place. A vascular graft 10 is then mounted on the catheter 30 and reintroduced so that the compressed vascular graft lies within the fabric liner leg 28 while covered with sheath 42, as illustrated in FIG. 9. The sheath 42 is then withdrawn so that the vascular graft 10 will expand both within the leg 28 and the left iliac LI, as illustrated in FIG. 10. The catheter 30 is then withdrawn, and the guidewire is transferred from the left iliac LI to the right iliac RI. Alternatively, a separate guidewire could be introduced. Catheter 30 is then reintroduced over the guidewire with sheath 42 covering a second vascular graft 10 and advanced into the right iliac, as illustrated in FIG. 11. The sheath 42 is then withdrawn, allowing the second vascular graft 10 to expand within both the right iliac RI and the second leg 26 of the fabric liner. The completed bifurcated graft structure is then in place, as illustrated in FIG. 12, and the guidewire GW, catheter 30, and introducer sheath 50 may then be withdrawn.

Femoral access and retrograde placement of the graft structures of the present invention will be possible although such an approach is not presently preferred.

Positioning and repositioning of the stent-graft structure of the present invention can be facilitated by use of an ultrasonic imaging catheter or guidewire, such as the guidewires described in U.S. Pat. No. 5,095,911 and PCT WO 93/16642. Such ultrasonic guidewires can be used in place of the conventional guidewire GW illustrated in FIGS. 7-12, typically being sealed by a hemostasis valve at the proximal end of the delivery catheter 30. Locking means, clamps, markings, and the like, may be provided on either or both of the delivery catheter 30 and the imaging guidewire to assure proper positioning of the ultrasonic transducer within the stent-graft structure during the placement procedure. The aneurysm or other anomaly being treated can then be precisely located prior to release of the stent-graft 10. After partial placement, proper location of the stent-graft 10 can be confirmed with the ultrasonic imaging device. If the position is not correct, the stent-graft 10 can be drawn back into the sheath 42, and the stent-graft can be repositioned prior to complete release. The use of an ultrasonic imaging guidewire is advantageous since there is no need to exchange the guidewire for a separate ultrasonic imaging catheter.

Although the foregoing invention has been described in some detail by way of illustration and example, for purposes of clarity of understanding, it will be obvious that certain changes and modifications may be practiced within the scope of the appended claims.

What is claimed is:

1. A method for introducing a vascular graft into a primary artery which divides into first and second branch arteries, said method comprising:
    introducing and deploying a bifurcated structure including an anchor section and first and second connector sections so that the anchor section is disposed within the primary artery and the first and second connector sections extend toward the first and second branch arteries and thereafter;
    introducing a first tubular graft into the first connector section and anchoring said first tubular graft to extend between the first connector section and the first branch artery to form a first continuous flow path from the primary artery to the first branch artery; and
    introducing a second tubular graft into the second connector section and anchoring said second tubular graft to extend between the second connector section and the second branch artery to form a second continuous flow path from the primary artery to the second branch artery.

2. A method as in claim 1, wherein the primary artery is an aorta, the first branch artery is a right iliac, and the second branch artery is a left iliac.

3. A method as in claim 1, wherein the anchor section of the bifurcated structure is radially compressed while being introduced.

4. A method as in claim 3, wherein the anchor section is composed of a resilient material, said method further comprising releasing the radially compressed anchor section at a target location with the primary artery.

5. A method as in claim 1, wherein the bifurcated structure is introduced through the primary artery in an antegrade direction.

6. A method as in claim 1, wherein the bifurcated structure is introduced through a branch artery in a retrograde direction.

7. A method as in claim 1, wherein the first tubular graft is radially compressed while being introduced.

8. A method as in claim 7, wherein the first tubular graft is composed of a resilient material, said method further comprising releasing the radially compressed graft to anchor simultaneously within the first connector and the first branch artery.

9. A method as in claim 1, wherein the first tubular graft is introduced through the primary artery in an antegrade direction.

10. A method as in claim 1, wherein the first tubular graft is introduced through a branch artery in a retrograde direction.

11. A method as in claim 1, wherein the second tubular graft is radially compressed while being introduced.

12. A method as in claim 11, wherein the second tubular graft is composed of a resilient material, said method further comprising releasing the radially compressed graft to anchor simultaneously within the second connector and the second branch artery.

13. A method as in claim 1, wherein the second tubular graft is introduced through the primary artery in an antegrade direction.

14. A method as in claim 1, wherein the second tubular graft is introduced through a branch artery in a retrograde direction.

15. A method for treating an aneurysm by introducing a vascular graft into a primary artery which branches into first and second branch arteries, said method comprising:
    introducing into a patient's vasculature an anchor section and first tubular graft of the vascular graft so that the anchor section is disposed within the primary artery and the first tubular graft is at least partially disposed within the first branch artery to form a first continuous flow path from the primary artery to the first branch artery; and
    securing a second tubular graft to the anchor section via a connector leg of the anchor section to form a second continuous flow path from the primary artery to the second branch artery, wherein each of the grafts comprises a tubular frame and a liner.

16. A method as in claim 15, wherein the primary artery is an aorta, the first branch artery is a right iliac, and the second branch artery is a left iliac.

17. A method as in claim 15, wherein the anchor section and first tubular graft of the vascular graft are radially compressed while being introduced.

18. A method as in claim 17, wherein the anchor section and first tubular graft of the vascular graft are resilient, said introducing step comprising releasing the radially compressed anchor section and first tubular graft at a target location with the vasculature.

19. A method as in claim 18, wherein the anchor section and first tubular graft of the vascular graft are introduced through the primary artery in an antegrade direction.

20. A method as in claim 18, wherein the anchor section and first tubular graft of the vascular graft are introduced through a branch artery in a retrograde direction.

21. A method as in claim 18, wherein the second tubular graft is radially compressed while being introduced.

22. A method as in claim 21, wherein the second tubular graft is resilient, said method further comprising releasing the radially compressed second tubular graft to anchor within the connector leg on the anchor section.

23. A method as in claim 22, wherein the second tubular graft is introduced through the primary artery in an antegrade direction.

24. A method as in claim 22, wherein the second tubular graft is introduced through a branch artery in a retrograde direction.

25. A method as in claim 15, wherein the introducing step comprises securing the first tubular graft to the anchor section of the vascular graft after the anchor section has been disposed within the primary artery.

26. A method as in claim 25, wherein the first tubular graft is secured to the anchor section via a second connector leg of the anchor section.

27. A method as in claim 26, wherein the first tubular graft is resilient and wherein the securing of the first tubular graft to the anchor section comprises releasing the first tubular graft from a compressed configuration to expand within the second connector leg and the first branch artery.

28. A method as in claim 27, wherein the second tubular graft is resilient and wherein the securing of the second tubular graft to the anchor section comprises releasing the second tubular graft from a compressed configuration to expand within its respective connector leg and the second branch artery.

29. A method as in claim 25, wherein the primary artery is an aorta, the first branch artery is a right iliac, and the second branch artery is a left iliac.

30. A method as in claim 29, wherein the second tubular graft is resilient and wherein the securing of the second tubular graft to the anchor section comprises releasing the second tubular graft from a compressed configuration to expand within the connector leg and the left iliac.

31. A method as in claim 25, wherein the anchor section of the vascular graft is radially compressed while being introduced.

32. A method as in claim 31, wherein the anchor section is resilient, said introducing step comprising releasing the radially compressed anchor section at a target location with the vasculature.

33. A method as in claim 32, wherein the anchor section of the vascular graft is introduced through the primary artery in an antegrade direction.

34. A method as in claim 32, wherein the anchor section of the vascular graft is introduced through a branch artery in a retrograde direction.

35. A method as in claim 25, wherein the first tubular graft is radially compressed while being introduced.

36. A method as in claim 35, wherein the first tubular graft is resilient, said introducing step comprising releasing the radially compressed first tubular graft to anchor within a second connector leg on the anchor section.

37. A method as in claim 36, wherein the first tubular graft is introduced through the primary artery in an antegrade direction.

38. A method as in claim 36, wherein the first tubular graft is introduced through a branch artery in a retrograde direction.

39. A method as in claim 36, wherein the second tubular graft is radially compressed while being introduced.

40. A method as in claim 39, wherein the second tubular graft is resilient, said method further comprising releasing the radially compressed second tubular graft to anchor simultaneously within the connector leg on the anchor section and the second branch artery.

41. A method as in claim 40, wherein the second tubular graft is introduced through the primary artery in an antegrade direction.

42. A method as in claim 40, wherein the second tubular graft is introduced through a branch artery in a retrograde direction.

* * * * *

UNITED STATES PATENT AND TRADEMARK OFFICE
CERTIFICATE OF CORRECTION

PATENT NO. : 8,206,427 B1  
APPLICATION NO. : 08/463836  
DATED : June 26, 2012  
INVENTOR(S) : Ryan et al.

Page 1 of 1

It is certified that error appears in the above-identified patent and that said Letters Patent is hereby corrected as shown below:

On the Title Page:

Abstract, lines 2 and 3

"...portion of the frames lumen..."

should be changed to

--portion of the framed lumen--

In the Claims:

Column 14, line 9

"...as in claim 36, wherein..."

should be changed to

--as in claim 25, wherein--

Signed and Sealed this  
Sixteenth Day of July, 2013

Teresa Stanek Rea  
*Acting Director of the United States Patent and Trademark Office*